US007648835B2

(12) United States Patent
Breidford et al.

(10) Patent No.: US 7,648,835 B2
(45) Date of Patent: *Jan. 19, 2010

(54) SYSTEM AND METHOD FOR HEATING, COOLING AND HEAT CYCLING ON MICROFLUIDIC DEVICE

(75) Inventors: Wayne L. Breidford, Seattle, WA (US); Christy A. Lancaster, Seattle, WA (US); Jon W. Hayenga, Redmond, WA (US); Ronald L. Bardell, St. Louis Park, MN (US); Jeffrey F. Tonn, Tacoma, WA (US); Bernhard H. Weigl, Seattle, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/199,613

(22) Filed: Aug. 27, 2008

(65) Prior Publication Data

US 2009/0081771 A1 Mar. 26, 2009

Related U.S. Application Data

(63) Continuation-in-part of application No. 10/862,826, filed on Jun. 7, 2004, now Pat. No. 7,544,506.

(60) Provisional application No. 60/476,352, filed on Jun. 6, 2003.

(51) Int. Cl.
*C12M 1/34* (2006.01)
*C12M 3/00* (2006.01)

(52) U.S. Cl. .................................................. 435/288.5

(58) Field of Classification Search ............... 435/288.5
See application file for complete search history.

(56) References Cited

U.S. PATENT DOCUMENTS 5,498,392 A 3/1996 Wilding et al. ............. 422/68.1

(Continued)

FOREIGN PATENT DOCUMENTS

EP 1125630 A2 8/2001

(Continued)

OTHER PUBLICATIONS

Anderson et al., "A miniature integrated device for automated multistep genetic assays," *Nucleic Acids Research 28*(12):e60i-e60vi, Jun. 15, 2000.

(Continued)

*Primary Examiner*—Walter D Griffin
*Assistant Examiner*—Lydia Edwards
(74) *Attorney, Agent, or Firm*—Seed IP Law Group PLLC

(57) ABSTRACT

An integrated heat exchange system on a microfluidic card. According to one aspect of the invention, the portable microfluidic card has a heating, cooling and heat cycling system on-board such that the card can be used portably. The microfluidic card includes one or more reservoirs containing exothermic or endothermic material. Once the chemical process of the reservoir material is activated, the reservoir provides heat or cooling to specific locations of the microfluidic card. Multiple reservoirs may be included on a single card to provide varying temperatures. The assay chemicals can be moved to the various reservoirs to create a thermal cycle useful in many biological reactions, for example, Polymerase Chain Reaction (PCR) or rtPCR. According to another aspect of the invention, the integrated heat exchanger is an adjacent microfluidic circuit containing fluid that is either independently heated or cooled, or is an exothermic or endothermic material, such that the fluid in the adjacent circuit imparts a change in temperature to the assay fluid in an independent circuit. According to yet another aspect of the invention, a thermal electric cooler (TEC) is used for thermocycling the amplification chamber of a disposable microfluidic card.

12 Claims, 32 Drawing Sheets

U.S. PATENT DOCUMENTS

| | | | | |
|---|---|---|---|---|
| 5,587,128 | A | 12/1996 | Wilding et al. | 422/50 |
| 5,639,423 | A | 6/1997 | Northrup et al. | 122/50 |
| 5,716,852 | A | 2/1998 | Yager et al. | 436/172 |
| 5,724,404 | A | 3/1998 | Garcia et al. | 379/34 |
| 5,726,026 | A | 3/1998 | Wilding et al. | 435/7.21 |
| 5,726,751 | A | 3/1998 | Altendorf et al. | 356/246 |
| 5,747,349 | A | 5/1998 | van den Engh et al. | 436/172 |
| 5,748,827 | A | 5/1998 | Holl et al. | 385/134 |
| 5,922,210 | A | 7/1999 | Brody et al. | 210/767 |
| 5,932,100 | A | 8/1999 | Yager et al. | 210/634 |
| 5,939,312 | A | 8/1999 | Baier et al. | 435/287.2 |
| 5,948,684 | A | 9/1999 | Weigl et al. | 436/52 |
| 5,955,029 | A | 9/1999 | Wilding et al. | 422/68.1 |
| 5,958,349 | A | 9/1999 | Petersen et al. | 422/198 |
| 5,971,158 | A | 10/1999 | Yager et al. | 209/155 |
| 5,972,710 | A | 10/1999 | Weigl et al. | 436/34 |
| 5,974,867 | A | 11/1999 | Forster et al. | 73/61.41 |
| 6,007,775 | A | 12/1999 | Yager | 422/57 |
| 6,018,616 | A | 1/2000 | Schaper | 392/418 |
| 6,020,187 | A | 2/2000 | Tam | 435/287.2 |
| 6,054,277 | A | 4/2000 | Furcht et al. | 435/6 |
| 6,126,804 | A | 10/2000 | Andresen | 204/601 |
| 6,171,865 | B1 | 1/2001 | Weigl et al. | 436/52 |
| 6,180,372 | B1 | 1/2001 | Franzen | 435/91.1 |
| 6,192,596 | B1 | 2/2001 | Bennett et al. | 34/76 |
| 6,261,431 | B1 | 7/2001 | Mathies et al. | 204/601 |
| 6,303,343 | B1 | 10/2001 | Kopf-Sill | 435/91.1 |
| 6,387,290 | B1 | 5/2002 | Brody et al. | 216/99 |
| 6,403,037 | B1 | 6/2002 | Chang et al. | 422/68.1 |
| 6,420,143 | B1 | 7/2002 | Kopf-Sill | 435/91.1 |
| 6,432,695 | B1 | 8/2002 | Zou et al. | 435/287.2 |
| 6,440,725 | B1 | 8/2002 | Pourahmadi et al. | 435/288.5 |
| 6,509,186 | B1 | 1/2003 | Zou et al. | 435/286.1 |
| 6,541,274 | B2 | 4/2003 | Nagle et al. | 436/180 |
| 6,572,830 | B1 | 6/2003 | Burdon et al. | 422/186.29 |
| 6,613,560 | B1 | 9/2003 | Tso et al. | 435/287.2 |
| 6,699,713 | B2 | 3/2004 | Benett et al. | 435/287.2 |
| 6,762,049 | B2 | 7/2004 | Zou et al. | 435/287.2 |
| 6,787,338 | B2 | 9/2004 | Wittwer et al. | 435/91.2 |
| 6,960,437 | B2 | 11/2005 | Enzelberger et al. | 435/6 |
| 7,018,830 | B2 | 3/2006 | Wilding et al. | 435/287.1 |
| 7,544,506 | B2 * | 6/2009 | Breidford et al. | 435/288.5 |
| 2001/0046701 | A1 | 11/2001 | Schulte et al. | 435/287.2 |
| 2003/0138941 | A1 | 7/2003 | Gong et al. | 435/287.2 |
| 2004/0029258 | A1 | 2/2004 | Heaney et al. | 435/287.2 |
| 2004/0151629 | A1 | 8/2004 | Pease et al. | 422/68.1 |

FOREIGN PATENT DOCUMENTS

| | | | |
|---|---|---|---|
| WO | WO 97/27324 | A1 | 7/1997 |
| WO | WO 98/50147 | A1 | 11/1998 |
| WO | WO 99/12016 | A1 | 3/1999 |
| WO | WO 01/31053 | A1 | 5/2001 |
| WO | WO 01/41931 | A2 | 6/2001 |
| WO | WO 02/085777 | A2 | 10/2002 |
| WO | WO 03/004162 | A1 | 1/2003 |

OTHER PUBLICATIONS

Belgrader et al., "PCR Detection of Bacteria in Seven Minutes," *Science 284*(5413):449-450, Apr. 16, 1999.

Belgrader et al., "A Battery-Powered Notebook Thermal Cycler for Rapid Multiplex Real-Time PCR Analysis," *Analytical Chemistry 73*(2):286-289, Jan. 15, 2001.

Burke et al., "Microfabrication Technologies for Integrated Nucleic Acid Analysis," *Genome Research 7*:189-197, 1997.

Chartier et al., "Fabrication of an hybrid plastic-silicon microfluidic device for high-throughput Genotyping," *Proceedings of SPIE 4982*:208-219, 2003.

Chiou et al., "A Closed-Cycle Capillary Polymerase Chain Reaction Machine," *Analytical Chemistry 73*(9):2018-2021, May 1, 2001.

Dumer et al., "Remote Medical Evaluation and Diagnostics (RMED)—A Testbed for Hypertensive Patient Monitoring," *Computing Science and Statistics 32*:183-195, 2000.

Giordano et al., "Polymerase Chain Reaction in Polymeric Microchips: DNA Amplification in Less Than 240 Seconds," *Analytical Biochemistry 291*:124-132, 2001.

Hupert et al., "Polymer-Based Microfluidic Devices for Biomedical Applications," *Proceedings of SPIE 4982*:52-64, 2003.

Innis et al., "DNA sequencing with *Thermus aquaticus* DNA polymerase and direct sequencing of polymerase chain reaction-amplified DNA," *Proc. Natl. Acad. Sci USA 85*:9436-9440, Dec. 1988.

Khandurina et al., "Integrated System for Rapid PCR-Based DNA Analysis in Microfluidic Devices," *Analytical Chemistry 72*(13):2995-3000, Jul. 1, 2000.

Koh et al., "Integrating Polymerase Chain Reaction, Valving, and Electrophoresis in a Plastic Device for Bacterial Detection," *Analytical Chemistry 75*(17):4591-4598, Sep. 1, 2003.

Kopp et al., "Chemical Amplification: Continuous-Flow PCR on a Chip," *Science 280*:1046-1048, May 15, 1998.

Kricka et al., "Microchip PCR," *Anal. Bioanal. Chem. 377*:820-825, 2003.

Lagally et al., "Fully integrated PCR-capillary electrophoresis microsystem for DNA analysis," *Lab on a Chip 1*:102-107, 2001.

Liu et al., "Self-Contained, Fully Integrated Biochip for Sample Preparation, Polymerase Chain Reaction Amplification, and DNA Microarray Detection," *Analytical Chemistry 76*(7):1824-1831, Apr. 1, 2004.

Liu et al., "A nanoliter rotary device for polymerase chain reaction," *Electrophoresis 23*:1531-1536, 2002.

Liu et al., "DNA Amplification and Hybridization Assays in Integrated Plastic Monolithic Devices," *Analytical Chemistry 74*(13):3063-3070, Jul. 1, 2002.

Mao et al., "A Microfluidic Device with a Linear Temperature Gradient for Parallel and Combinatorial Measurements," *J. Am. Chem. Soc. 124*:4432-4435, 2002.

Mitchell et al., "Modeling and Validation of a Molded Polycarbonate Continuous Flow Polymerase Chain Reaction Device," *Proceedings of SPIE 4982*:83-98, 2003.

Nakano et al., "High Speed Polymerase Chain Reaction in Constant Flow," *Biosci. Biotech. Biochem 58*(2):349-352, 1994.

Panaro et al., "Surface Effects on PCR Reactions in Multichip Microfluidic Platforms," *Biomedical Microdevices 6*(1):75-80, 2004.

Tüdös et al., "Trends in miniaturized total analysis systems for point-of-care testing in clinical chemistry," *Lab on a Chip 1*:83-95, 2001.

Wilding et al., "PCR in a Silicon Microstructure," *Clinical Chemistry 40*(9):1815-1818, 1994.

Wittwer et al., "Minimizing the Time Required for DNA Amplification by Efficient Heat Transfer to Small Samples," *Analytical Biochemistry 186*:328-331, 1990.

Woolley et al., "Functional Integration of PCR Amplification and Capillary Electrophoresis in a Microfabricated DNA Analysis Device," *Analytical Chemistry 68*(23):4081-4086, Dec. 1, 1996.

Yang et al., "High sensitivity PCR assay in plastic micro reactors," *Lab on a Chip 2*:179-187, 2002.

Yuen et al., "Microchip Module for Blood Sample Preparation and Nucleic Acid Amplification Reactions," *Genome Research 11*:405-412, 2001.

Zou et al., "Micro-assembled multi-chamber thermal cycler for low-cost reaction chip thermal multiplexing," *Sensors and Actuators* A 102:114-121, 2002.

Zou et al., "Miniaturized Independently Controllable Multichamber Thermal Cycler," *IEEE Sensors Journal 3*(6):774-780, Dec. 2003.

* cited by examiner

Thermal Cycle Test Card in Manifold

Close-up of Test Card With Embedded (5 mil membrane) Thermocouples

TEC directly on SS table with no thermal interface material between the TEC and the card.

close up of above data.
Total cycle time 12.5 sec.

Card on TEC with heat sink and graphite pad

TEC on a heat sink and a graphite pad between the TEC and Amplification chamber.

A. Polymerase Chain Reaction (PCR) Temperature Profile

B. Nucleic Acid Sequence Based Analysis (NASBA) Temperature Profile

C. Reverse Transcriptase (rt) Temperature Profile

D. Loop Mediated Amplification (LAMP) Temperature Profile

SYSTEM AND METHOD FOR HEATING, COOLING AND HEAT CYCLING ON MICROFLUIDIC DEVICE

CROSS-REFERENCE TO RELATED APPLICATIONS

This is a continuation-in-part of U.S. patent application Ser. No. 10/862,826 filed Jun. 7, 2004 (now pending), which claims the benefit of U.S. Provisional Application No. 60/476,352, filed Jun. 6, 2003. Both of these applications are incorporated herein in their entireties.

BACKGROUND OF THE INVENTION

1. Field of the Invention

This invention relates to an integrated heater and cooler on a microfluidic device for use in thermocycling, and more particularly, to a portable microfluidic card with a heating, cooling and heat cycling system on-board. This invention further relates to a microfluidic card having an integrated heat exchanger circuit, or thermal electric cooler (TEC) for use in connection with a microfluidic device to provide thermocycling for use in, for example, PCR or rtPCR.

2. Description of the Related Art

Integrated microfluidic handling systems that provide control over nanoliter sized volumes of liquid are useful in both miniaturizing present analytical tests and handling the small sample sizes frequently used in biomedical testing. Entire chemical analyses can be preformed on a single microfluidic device. The microfluidic devices include components such as channels, valves, pumps, flow sensors, mixing chambers and optical detectors. Examples of these components and systems may be found in U.S. Pat. Nos. 5,932,100; 5,922,210; 6,387,290; 5,747,349; 5,748,827; 5,726,751; 5,724,404; 5,716,852; 5,974,867; 6,007,775; 5,972,710; 5,971,158; 5,948,684; and 6,171,865 (which patents are hereby incorporated by reference in their entirety).

The ability to perform analyses microfluidically provide substantial advantages of throughput, reagent consumption, and automatability. Another advantage of microfluidic systems is the ability to integrate large numbers of different operations in a single "lab-on-a-chip" device for performing processing of reactants for analysis and/or synthesis. One example of an operation that would benefit from the advantages of microfluidics is the Polymerase Chain Reaction, commonly known as PCR, or rtPCR, commonly known as reverse transcriptase-Polymerase Chain Reaction.

PCR is a technique used to amplify specific segments of DNA. In brief, DNA contacted with a solution containing the DNA polymerase, unbound nucleotide bases, and "primers" (i.e., short sequences of nucleotides that bind with an end of the desired DNA segment). Two primers are used. The first primer binds at one end of the desired segment on one of the two paired DNA strands, while the second primer binds at the other end but on the other DNA strand. The solution is heated to a temperature of about 95° C. to break the bonds between the strands of the DNA. Since the primers cannot bind the DNA strand at such high temperatures, the solution is cooled to about 55° C. At this temperature the primers bind or "anneal" to the separated strands. Since TAQ DNA polymerase works best at around 72° C., the temperature is again raised and the DNA polymerase quickly builds a new strand by joining the free nucleotide bases to the primers. When this process is repeated, a strand that was formed with one primer binds to the other primer, resulting in a new strand that is restricted solely to the desired segment. Thus the region of DNA between the primers is selectively replicated. Further repetitions of the process can produce billions of copies of a small segment of DNA in several hours.

Enabling the detection of a specific bacterium or virus, or a genetic disorder, PCR has become one of the most powerful tools available for human diagnostics. Since PCR can amplify even a single molecule of DNA, problems of contamination become paramount. To minimize the risk of contamination, many laboratories have needed to set up separate rooms to house their PCR machines.

rtPCR is short for reverse transcriptase-polymerase chain reaction. It is a technique in which an RNA strand is transcribed into a DNA complement to be able to subject it to PCR amplification. Transcribing an RNA strand into a DNA complement is termed reverse transcription and is done by the enzyme reverse transcriptase.

PCR based assays have three basic steps: isolation of DNA, amplification of DNA, and detection of DNA. The DNA isolation process in the past involved very tedious procedures and was a limiting factor for diagnostic PCR. With advancement in technology, DNA isolation procedures have become simplified such that DNA can be quickly extracted with reagent addition and centrifugation. Although simplified, traditional methods of isolation require the use of expensive and cumbersome equipment, including for example a non-refrigerated centrifuge of at least 1300 rpm with relative centrifugal force (RCF) of about 16000 g is required since. In addition, a good autoclavable set of micropipettes is also required for required for DNA extraction, as well as a variable speed heavy duty Vortex Mixer, a microwave oven for lysis of the cells, and a water bath for boiling and incubations.

After the DNA is isolated, a single DNA molecule can be amplified to as discussed above to more than a billion copies with the aid of a thermal cycler to change the temperature from for example about 96° C. to 55° C. to 72° C. in every cycle. In traditional PCR, use of glass capillaries as a reaction vessel for rapid heating and cooling of PCR reaction mixtures has been used to shorten the amplification time. However, even with these advancements, a system and method of PCR is needed that is simplified, minimizes the risk of contamination or human error, is portable, cost effective and accelerated. Once amplified, the DNA may be detected by any number of available techniques including, for example, with optical instruments. Detection of DNA can also be accomplished by electrophoresis or by liquid hybridization depending on whether confirmation or quantification is desired.

Although microfluidics has been used in a variety of applications, many technical issues with respect to performing the steps of isolation, amplification and detection remain for PCR to be effectively performed microfluidically. One difficulty is integration of a thermal cycler. Various attempts have been made to develop an adequate device for monitoring and changing the temperature on a microfluidic device. For example, International Patent Application PCT/US98/1791 is directed to a devices that controls and monitors temperature within microfluidic systems by applying electric currents to fluids to generate heat therein, as well as measure solution conductivity as a measure of fluid temperature.

Another system for controlling temperature on a microfluidic device is described in U.S. Pat. No. 6,541,274. This patent is directed to a reactor system having a plurality of reservoirs in a substrate. A heat exchanger is inserted in the reservoirs to control the temperature. Still others examples of existing devices for controlling temperature on a microfluidic device is with radiant heat as described in U.S. Pat. No. 6,018,616, and the temperature regulated controlled block as described in U.S. Pat. No. 6,020,187.

While significant advances have been made in the field of microfluidics generally, and PCR or rtPCR specifically, there remains a need in the art for microfluidic device that contains a thermal cycler, particularly in the context of microfluidic PCR or rtPCR. The present invention fulfils this need and provides further related advantages.

BRIEF SUMMARY OF THE INVENTION

The present invention is generally directed to a plastic microfluidic device with a heating, cooling and heat cycling system on-board, and to a microfluidic device having an integrated heat exchanger circuit or a thermal electric cooler (TEC).

In one embodiment, a microfluidic device is disclosed having a heating, cooling and heat cycling system on-board such that the device (e.g., in the form of a card) can be used portably. The microfluidic device includes one or more reservoirs containing exothermic or endothermic material. Once the chemical process of the reservoir material is activated, the reservoir provides heating or cooling to specific locations of the microfluidic card. Multiple reservoirs may be included on a single card to provide varying temperatures in various locations on the card. Any desired assay chemicals can be moved to the various reservoirs to create a thermal cycle useful in many biological reactions, including, for example, PCR.

In another embodiment, an integrated heat exchanger is disclosed. The exchanger is a microfluidic circuit containing fluid that is either independently heated or cooled, or is an exothermic or endothermic material, positioned adjacent to a microfluidic circuit containing assay fluid, such that the fluid in the adjacent circuit imparts a change in temperature to the assay fluid in an independent assay circuit. Both the heat exchanger circuit and the assay circuit are contained on the microfluidic device. The fluid in the heat exchanger circuit may be circulated by connecting the device to a manifold or instrumentation to provide a pumping means. The microfluidic card is made completely of plastic by lamination, molding, or by a combination of lamination and molding techniques.

In one embodiment of the present invention, a thermal electric cooler (TEC) is positioned adjacent to an amplification reservoir contained in the microfluidic card. A TEC controller is provided to manipulate the temperature of the TEC and in turn the amplification reservoir, and a voltage source is provided to provide power to the TEC. The amplification reservoir is fitted with a covering layer of polyethylene terephthalate, which encloses the amplification chamber and provides for heat exchange between the TEC and the contents of the amplification chamber.

These and other aspects of this invention will be apparent upon reference to the attached Figures and following detailed description.

DETAILED DESCRIPTION OF THE INVENTION

As noted above, the present invention is generally directed to a microfluidic device with a heating, cooling and heat cycling system on-board, a microfluidic device having an integrated heat exchanger circuit or a TEC used in connection with a microfluidic device to provide thermocycling.

According to one aspect of the invention, the portable microfluidic device is in the form of a card and has a heating, cooling and heat cycling system on-board such that the card can be used portably. (While generally discussed herein in the form of a planar "card", the microfluidic device of this invention may take any number of physical forms.) The microfluidic card includes one or more reservoirs containing exothermic or endothermic material. Once the chemical process of the reservoir material is activated, the reservoir provides heating or cooling to specific locations of the microfluidic card. Multiple reservoirs may be included on a single card to provide varying temperatures. The assay chemicals can be moved to the various reservoirs to create a thermal cycle useful in many biological reactions, including, for example, PCR.

Figure 1:
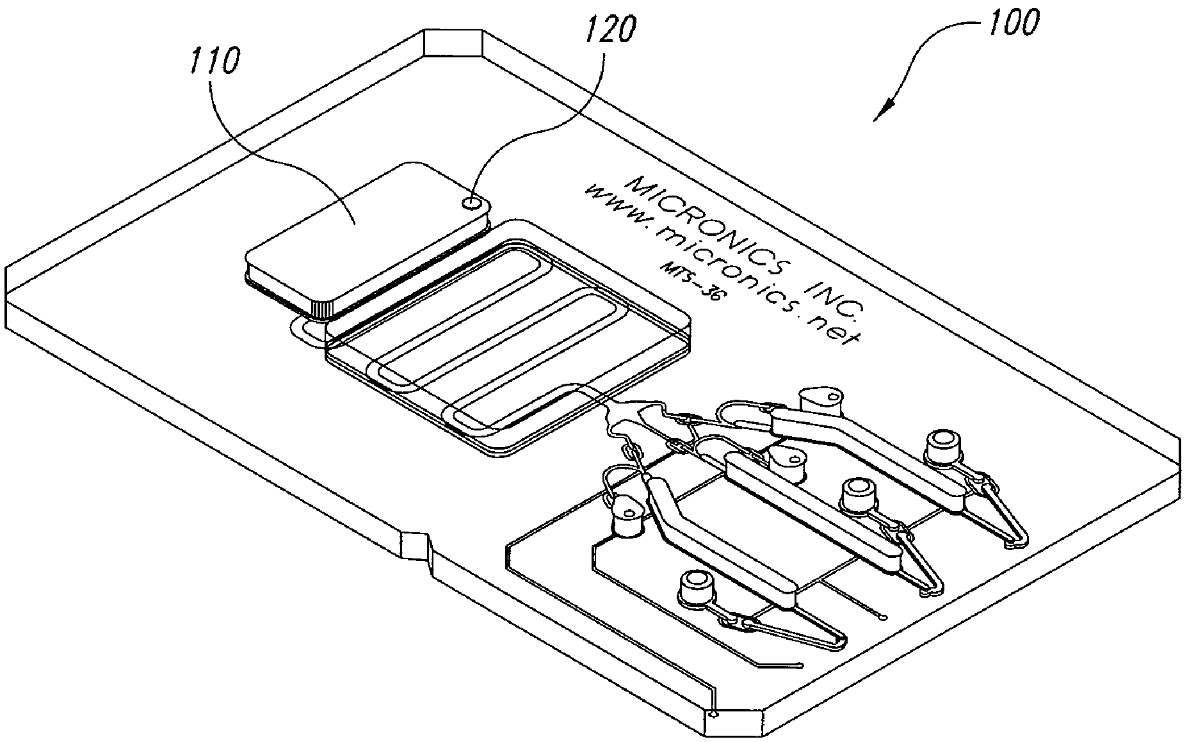
FIG. 1 illustrates a schematic view of a thermal cycling microfluidic device in accordance with principles of the present invention.

FIG. 1 illustrates one exemplary embodiment of the present invention. Microfluidic card 100 includes reservoir 110 for containing an exothermic or endothermic powder mixture. The reservoir 110 has a fill hole 120 that may be covered, for example by tape, until the heating or cooling cycle is initiated. Several chemical and physical processes between different components of solid or liquid mixtures are known to be significantly exothermic or endothermic. For example, a mixture of iron powder, activated charcoal powder, and cellulose can provide a constant temperature of 60° C. over several hours. On the other hand, the temperature of an aqueous solution decreases if ammonium chloride is added. There are hundreds of different mixtures that will, given the correct concentration, provide a certain heat absorption or output until the components are used up (i.e., the reaction is completed or the concentration of the components has equilibrated).

In the exemplary embodiment, an exothermic or endothermic mixture of material is contained in reservoir 110. Upon removal of the tape from the fill hole or inlet, air contacts the mixture and initiates a reaction in the mixture, causing the temperature above the reservoir to rise (or fall) depending upon the choice of material within the reservoir. In one example, a mixture of iron powder, activated charcoal powder, and cellulose was used and (after 10 minutes) was found to maintain a temperature of 62° C. (±3° C.) for 4 hours. Such mixtures can be placed at various places on a microfluidic card, and can, upon exposure to either air, moisture, or another chemical, initiate the heating (or cooling) process.

A practical application of such a card would include a passive or portable microfluidic card for performing biological reactions that needs incubations at a constant temperature, such as an immunoassay that would be kept at 37° C. for several minutes for incubation. Many other biological reactions are based on incubation of enzymes at 37° C. for minutes or hours. These include reverse transcriptases, DNA-dependent DNA polymerases, restriction enzymes, RNA-dependent DNA polymerases, loop-mediated isothermal amplification (LAMP), and nucleic acid sequence-based amplification (NASBA), among others.

Another embodiment would include multiple areas with different mixtures providing hot and/or cold zones on a microfluidic card over which a microfluidic circuit would carry the desired fluid over hot and/or cold areas in any order and for any contact time desired. For example, a thermal cycling experiment for nucleic acid amplification could be performed in this device. Different from current thermal cyclers that attempt to change the temperature at a static location where the samples are contained, this embodiment will circulate the sample to different locations of the card through microfluidics. These different locations would have the desired temperatures.

For example, a PCR card would have three locations at 95° C., 55° C. and 72° C. This application would result in shorter cycling times as the ramp-up times are much shorter (the times to go from one temperature to another). Ramping times contribute to more than 50% of the cycling times on typical thermal cyclers. Another benefit is the ability to use much smaller volumes. In a typical thermal cycler the typical volumes are 10-25 uL, mostly limited by the amount that can be measured by laboratory pipettes. In the practice of this invention, amplification of volumes as low as, for example, a microliter or even 100 mL may be achieved. Further, because of lower weight and power requirements, this invention allows the design of a handheld passive thermal cycling card that requires little or no external instrumentation for operation.

There are many benefits to a passive or portable PCR microfluidic card. The first two steps of a PCR-based assay (i.e., isolation and amplification) can now be integrated into a disposable plastic device the size of a credit card though microfluidics and microplumbing resulting in the following benefits: (1) minimization of contamination; (2) reduction of sample/reagent amounts; (3) reduction in assay time; (4) portability (including point of care application); (5) simplicity; (6) back and front integration (e.g., combination of sample preparation and analysis on single card); and (7) elimination of multiple analytical systems.

Specifically with respect to instruments and equipment, there are many advantages to a PCR-based microfluidic card. In a PCR card, the steps previously required for DNA extraction which required a non-refrigerated centrifuge may be substituted by DNA separation through mixing, molecular diffusion and the use of embedded membranes or matrices. Similarly, for RNA isolation, the instruments will be substituted, and in addition, the temperature can be changed through the use of chemical reactants. Micro-pipettes are eliminated with a microfluidic PCR card as fluids are moved by hydrostatic pressure. Mixing is performed through diffusion, and cell lysis is performed by mixing with lysing reagents, not in a microwave oven. A water bath is similarly not needed, as temperature may be changed through chemical reactants in the card. With respect to DNA amplification, in the PCR card of the present invention, thermal cyclers are replaced by either on-board reservoirs or microfluidic circuits adjacent to the assay circuit. Further, significant reduction of space is provided as all of the steps will occur in the PCR card under contained sterile conditions, and separate clean rooms will not be required.

Fluid Heating and Cooling: Heat Exchanger

According to another aspect of the invention, the integrated, heat exchanger is a microfluidic circuit containing fluid that is either independently heated or cooled, or is an exothermic or endothermic material positioned adjacent to a microfluidic circuit containing assay fluid, such that the fluid in the adjacent circuit imparts a change in temperature to the assay fluid in an independent circuit. Both the heat exchanger circuit and the assay containing circuit are contained on the microfluidic card. The fluid in the heat exchanger circuit may be circulated by connecting the card to a manifold of instrumentation to provide a pumping means.

In any exemplary embodiment of a microfluidic card, integral heating and cooling includes two or more pump and valve-controlled microfluidic circuits in close proximity (e.g., one on top of the other or otherwise adjacent). One circuit allows the interdiffusion of specific quantities of a two-part heating or cooling mixture, and the other is a microfluidic circuit containing the assay chemicals that require heating and/or cooling. By controlling the interdiffusion of the components of a heating mixture, for example, the exact temperature can be adjusted, and kept for as long as the two components of the heating mixture are flowing.

Figure 2:
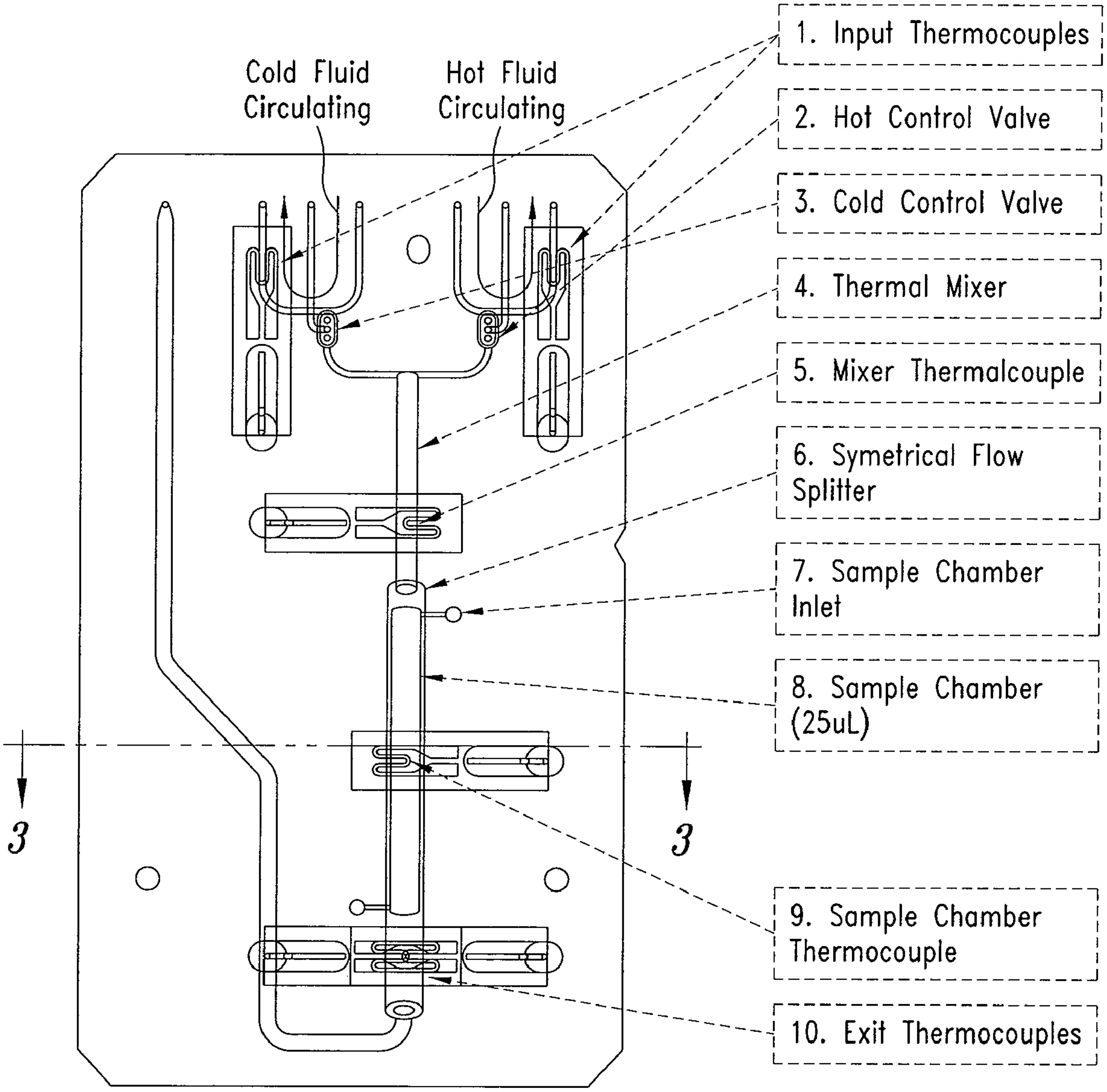
FIG. 2 illustrates a plan view of one embodiment of a thermo cycling microfluidic device of the present invention in accordance with principles of the present invention.

One embodiment of such a rapid thermal cycler is the microfluidic card shown in FIG. 2. This configuration enables thermal transition capability of PCR size thermal changes more than four times faster than standard thermal cyclers. These results have been experimentally determined and are demonstrated with real data showing ramping rates of up to 17° C./sec showing 50° C. change in less than 3 seconds, or a ramping rate of 17° C. per second.

There are numerous operational, manufacturing and technological advantages to a microfluidic card with active microfluidic circuits for providing heating and/or cooling. For example, these systems require relatively low power, the microfluidic card is of small size and the heating/cooling unit is targeted to be, for example, 4 cubic inches, any intermediate temperature in the aqueous range can be achieved with an appropriate thermal controller (0-100° C.), and/or aqueous samples can be frozen as well as boiled. Further, the microfluidic valve capability, given their small size and the thermal insulation properties of the plastics used, provides the ability to rapidly change temperatures without having to change temperatures of large thermal masses in valves and card plastic. Similarly, low thermal mass allows very rapid thermal changes.

Figure 3:
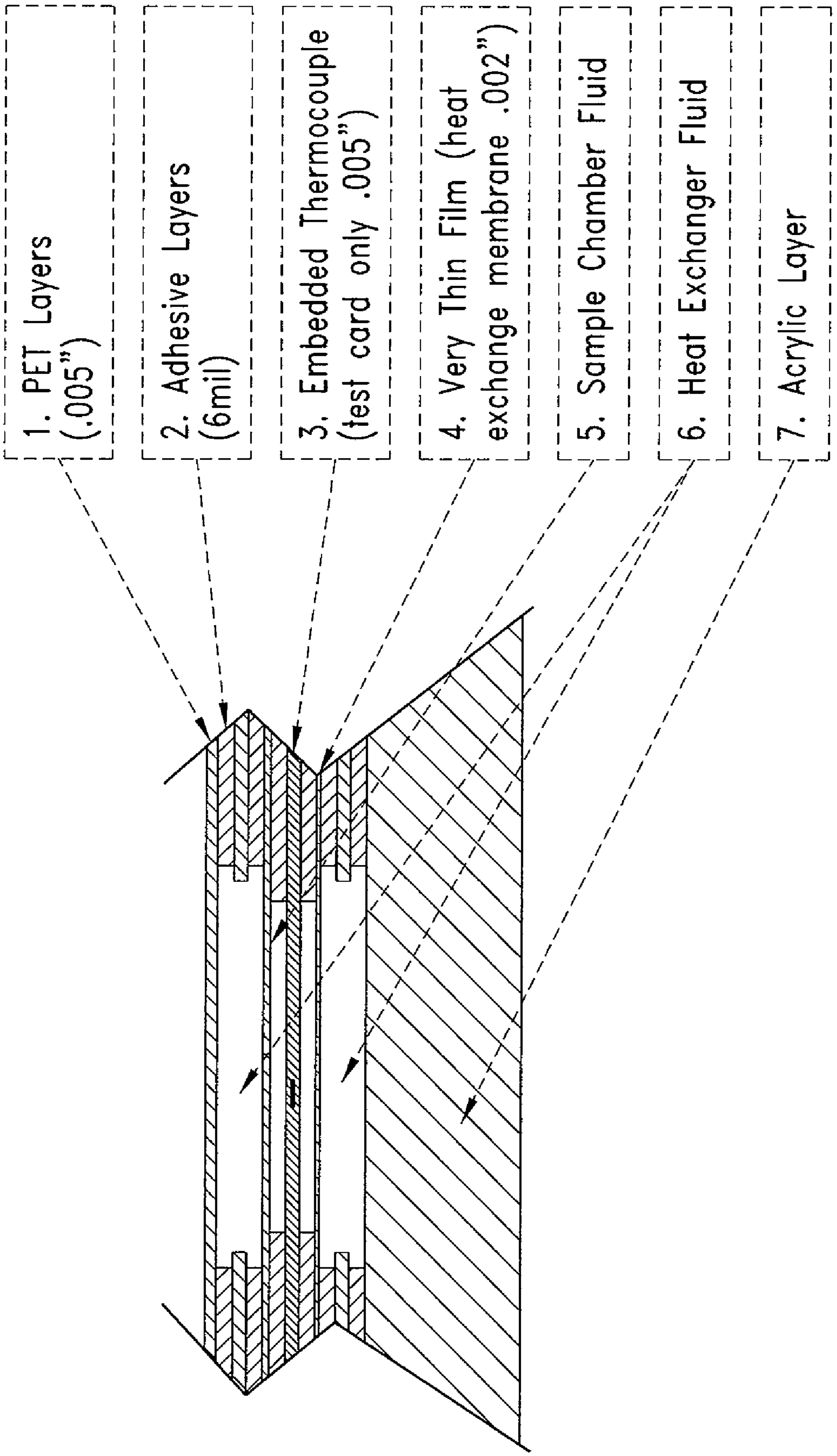
FIG. 3 illustrates a cross sectional view of the microfluidic device of FIG. 2 along lines 3A-3A in accordance with principles of the present invention.
Figure 4A:
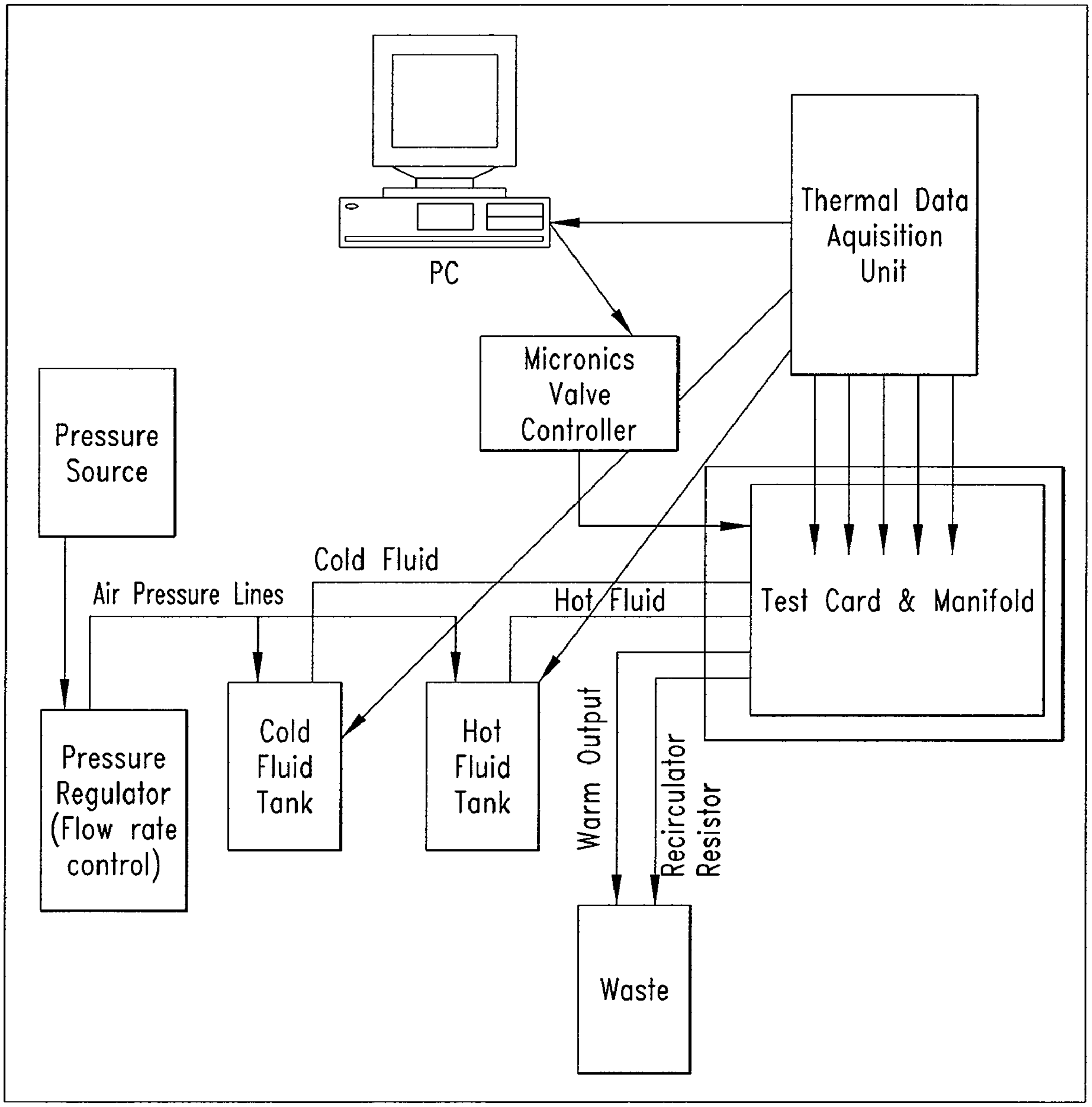
FIGS. 4A-C illustrate a flow chart and photographs of a thermal cycling microfluidic device in a manifold in accordance with principles of the present invention.
Figure 4B:
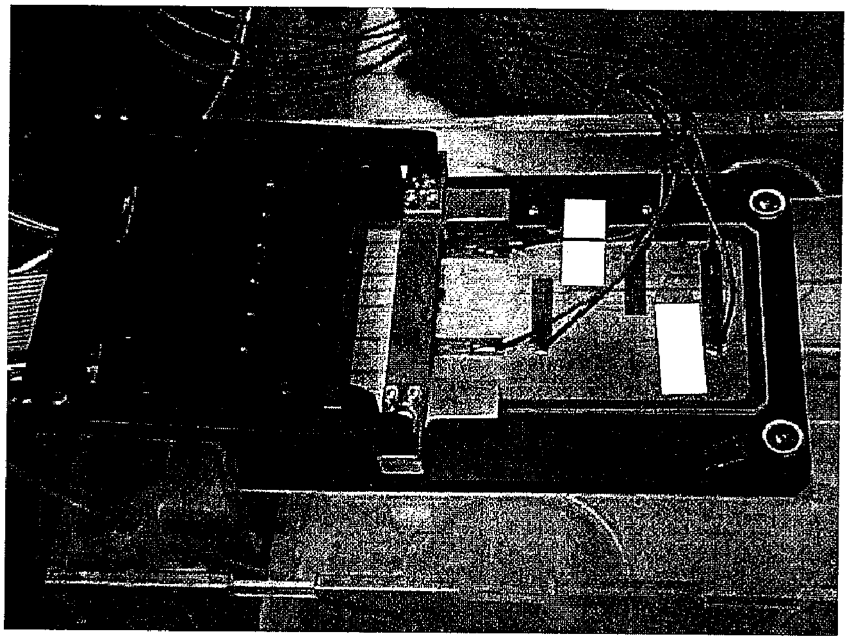
Figure 4C:
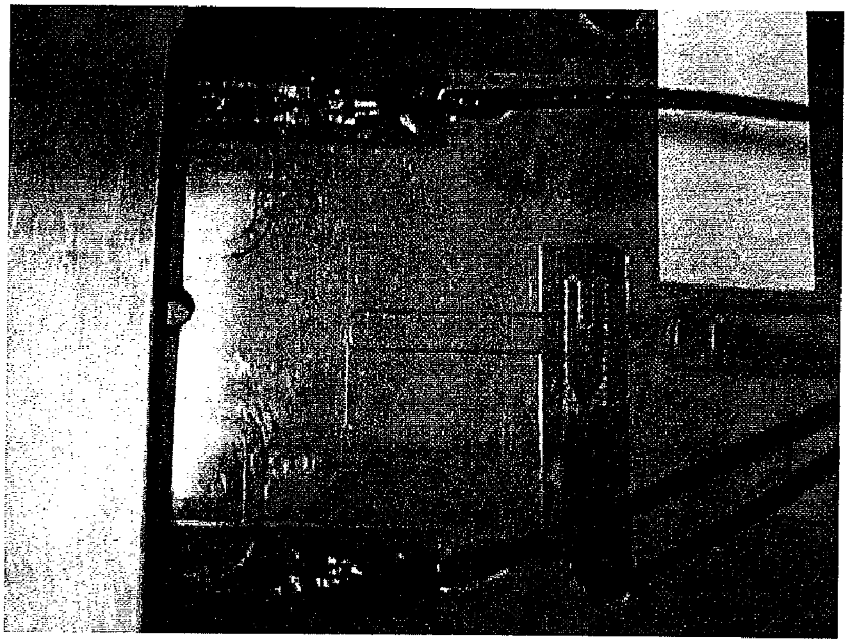

FIG. 2 is a top view of one embodiment of a thermal cycling heat exchanger test card is depicted. This specially designed and fabricated card was built to measure the effectiveness of the heating and cooling scheme. FIG. 3 is a cross section taken along line 3A-3A of the test card shown in FIG. 2. FIG. 4A is a flow chart of the test card. FIG. 4B is a photograph of the test card inserted in a manifold. FIG. 4° C. is a photograph of the test card with embedded thermocouples.

In FIG. 5 through FIG. 8, the following are definitions of the figure legends:

ColdSrc-Indicates the temperature of the cold fluid in the cold fluid storage tank (in this case ice water at approximately 0.3° C.).

HotSrc-Indicates the temperature of the hot fluid in the hot fluid storage tank (in this case this was water heated to approximately 80° C.).

ColdIN-Is the measured temperature of the circulating cold water at the card inlet. This is an indicator of the rise in temperature of the cold fluid on its way to the card under test. This temperature rise is not critical for these experiments, but will be minimized with design of a small closely coupled fluid heater/cooler.

HotIN-Is the measured temperature of the circulating hot water at the card inlet. This is an indicator of the drop in temperature of the hot fluid (to ambient room temp) on its way to the card under test.

Mixer-The temperature of the chamber used to equalize the mix of hot and cold fluids before running the fluid through the channels directly above and below the sample fluid. This indicates the time of commanded change in temperature by indicating the change in state of either the hot or cold fluid valves and of the temperature of the hot and cold mixture.

Chamber-The temperature of the embedded thermocouple in the 25 micro liter sample chamber of the test card. This is the measured thermal response of the sample.

Figure 5:
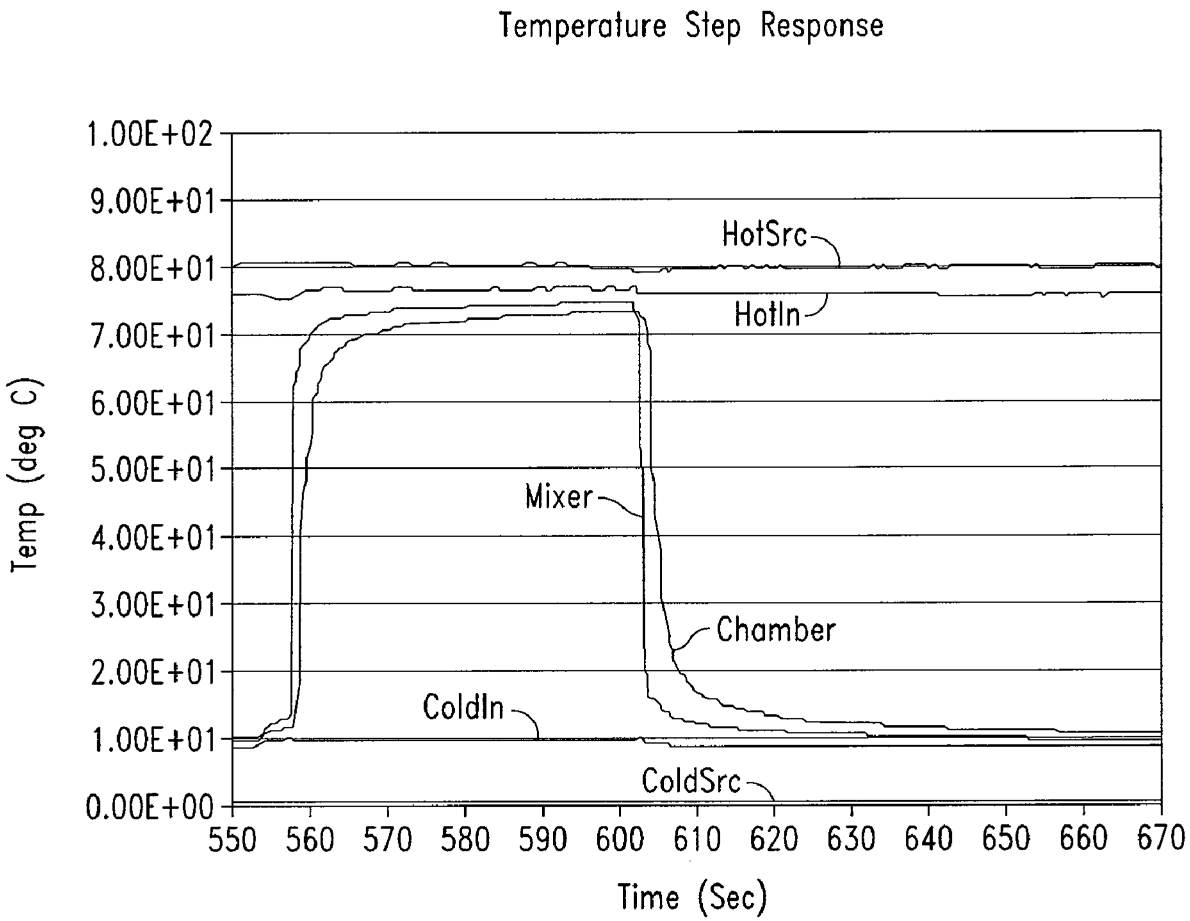
FIG. 5 is a graph illustrating the thermal chamber step response over time in accordance with principles of the present invention.

FIG. 5 is a graph of the thermal chamber temperature step response. The step response is a standard linear system characterization of a control system. The open loop step response shown in FIG. 5 indicates a rise and fall time that can characterize the maximum cycle times for the structure we are testing. The step response is derived by equilibrating the chamber temperature with the cold fluid valve open, and then closing the cold fluid valve and at the same time opening the hot fluid valve for 50 seconds and then closing the hot fluid valve and again opening the cold fluid valve.

Figure 6:
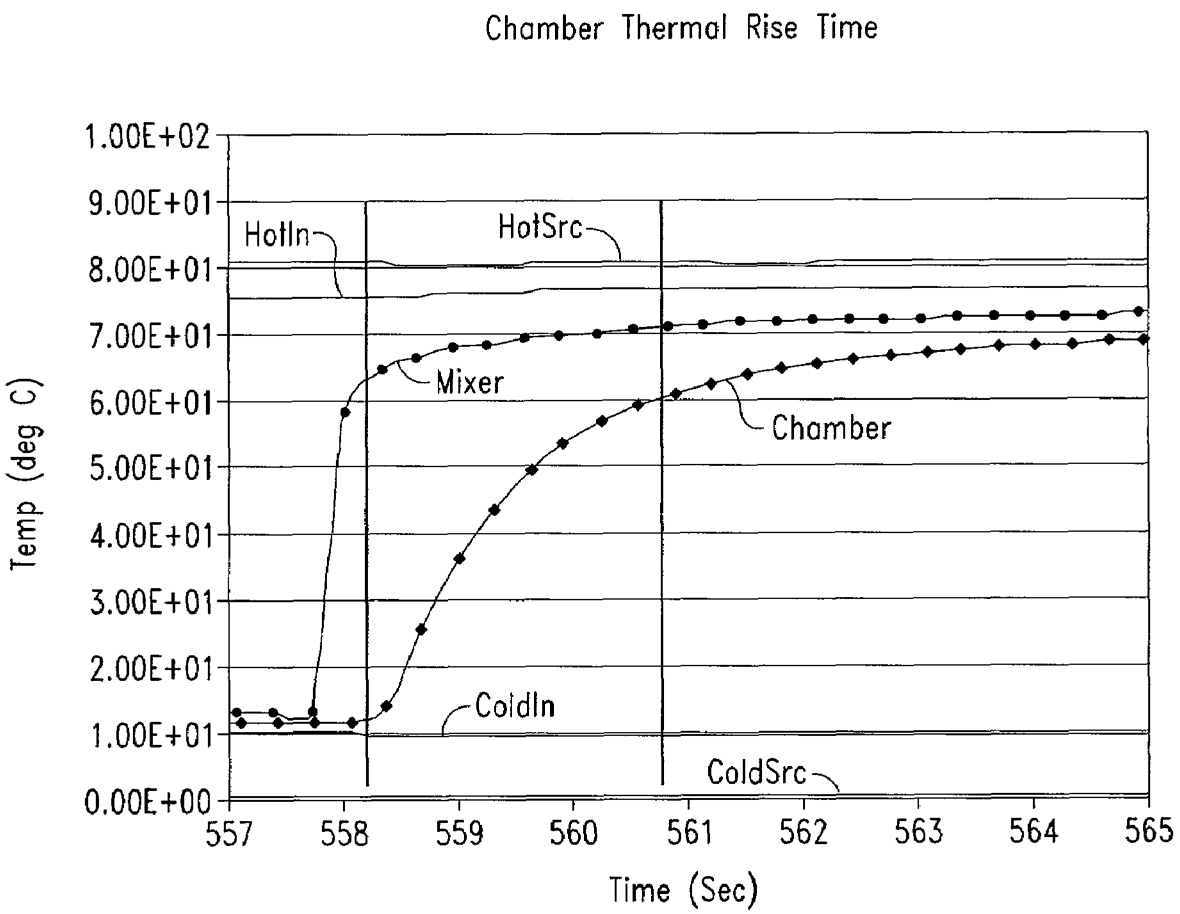
FIG. 6 is a graph illustrating the thermal rise over time of the thermal chamber in accordance with principles of the present invention.

FIG. 6 is a graph of the chamber's thermal rise over time. The rise time of the chamber temperature response is delayed by about 1 second from the thermal rise of the mixer heat exchanger fluid. This is mostly accounted for by the flow speed of the fluid and the separation of the thermocouples. Flow rate can be increased for reduced delay from driving temperature to response temperature. In the configuration of the card designed, a 50° C. sample temperature rise is effected within 3 seconds. One protocol for PCR calls for temperature plateaus of 50° C. transitioning to 95° C. to 75° C. and back to 50° C. With correctly heated and controlled driving fluids, this positive thermal rise could be achieved in less than 3 seconds.

Figure 7:
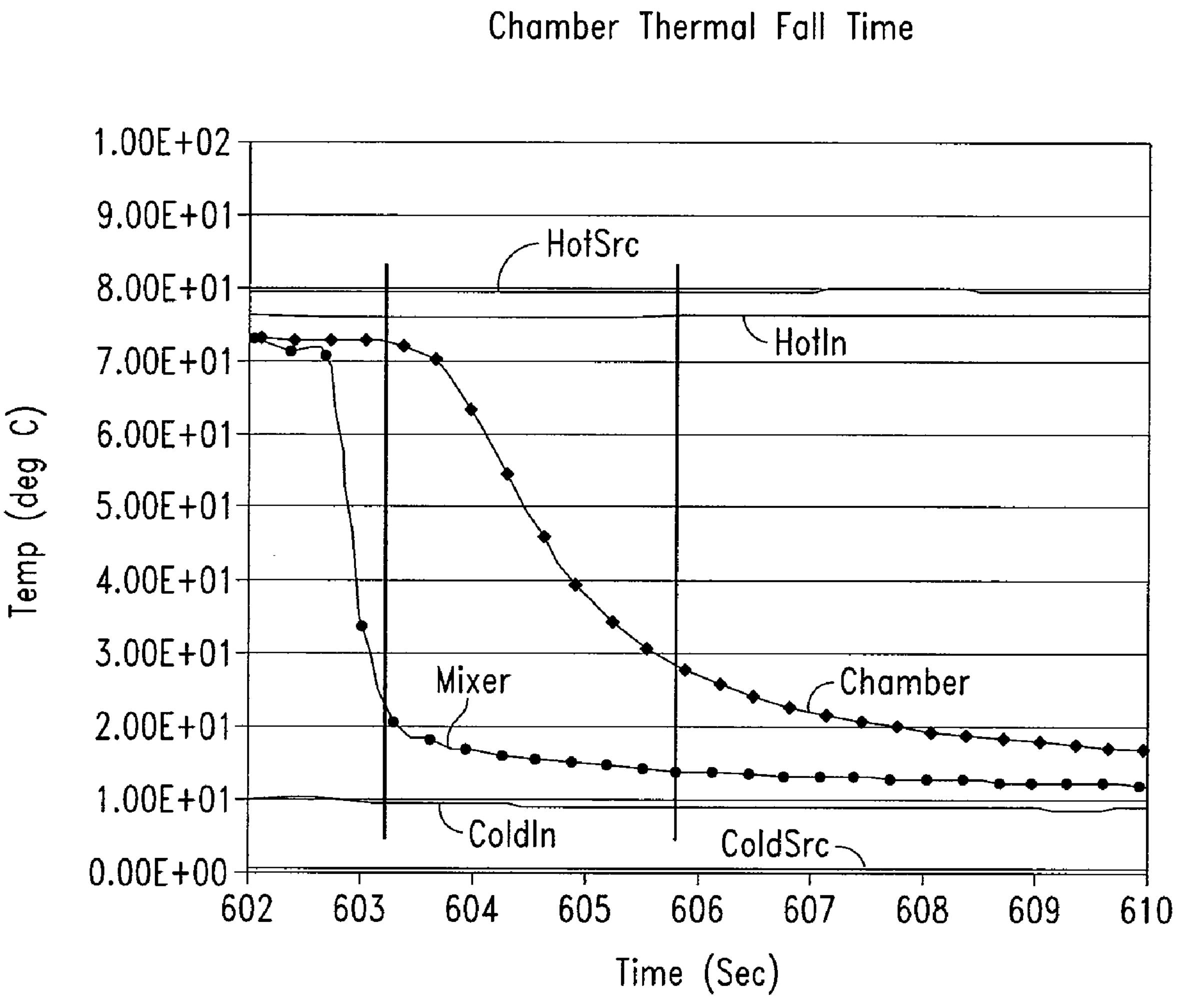
FIG. 7 is a graph illustrating the thermal fall over time of the thermal chamber in accordance with principles of the present invention.

FIG. 7 is a graph of the chamber's thermal fall over time. The fall time for the thermal exchange achieves a 40° C. temperature drop in less than 3 seconds. Again, in a typical PCR protocol, a thermal drop of 20-30° C. is required. With an appropriately designed closed loop thermal flow controller, this 25 uL sample could be thermally cycled through three PCR temperatures in approximately 10 seconds, thus allowing for the thirty or so cycles of PCR to occur in about 5 minutes.

Figure 8:
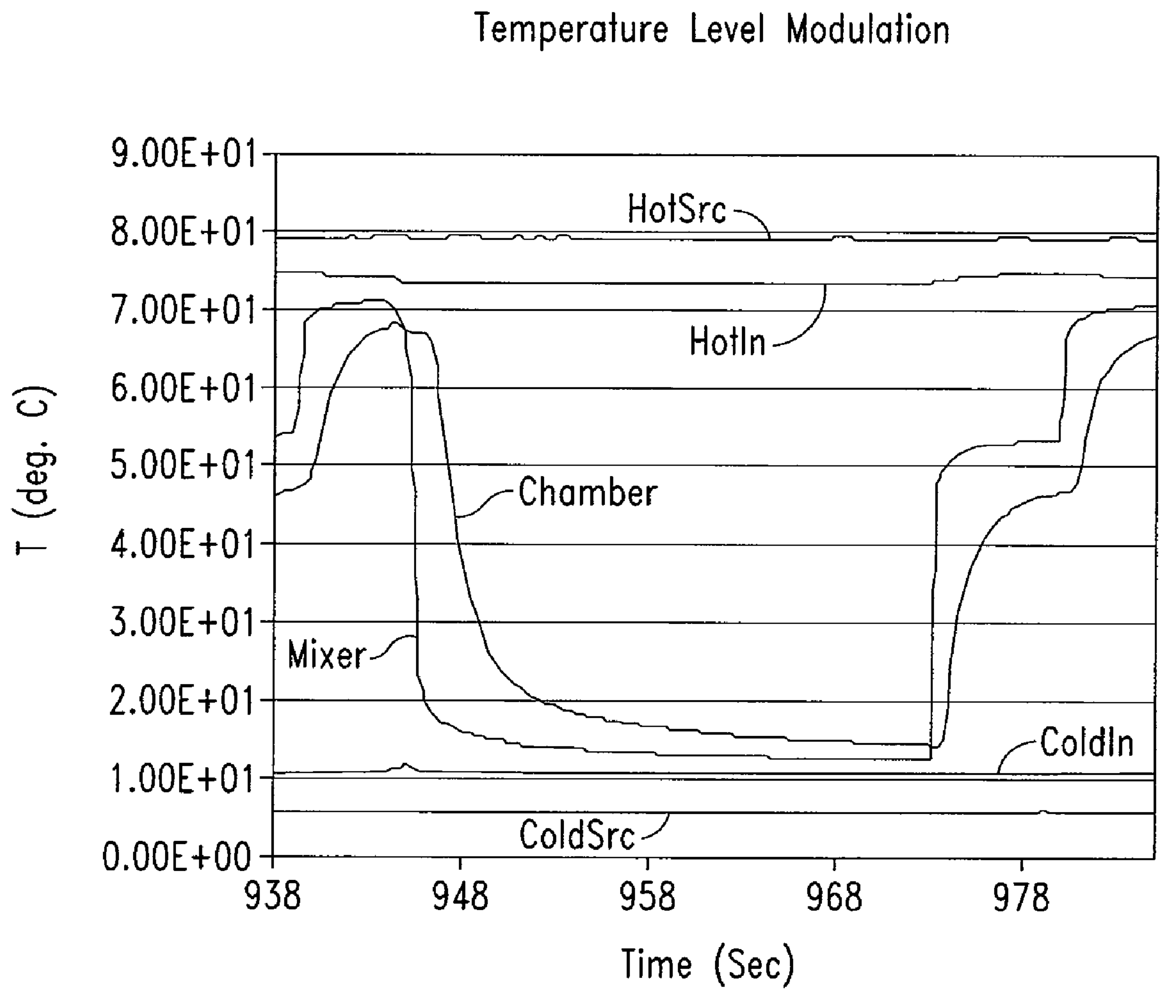
FIG. 8 is a graph illustrating a three level PCR temperature modulation versus time in accordance with principles of the present invention.

FIG. 8 is a graph of the three level-type (e.g., PCR) modulation. A simple open loop three level temperature cycle is demonstrated by opening the hot and cold fluid valves simultaneously to achieve an intermediate temperature. This demonstrates the ability of the valving system to achieve intermediate temperatures between the hot and cold fluid limits. A valve control system utilizing a duty cycle modulation of the hot and cold valves with an appropriately designed mixer may achieve any intermediate temperature. It can also allow tailoring of the driving temperature function to achieve faster cycle times and stable intermediate temperatures.

Figure 9:
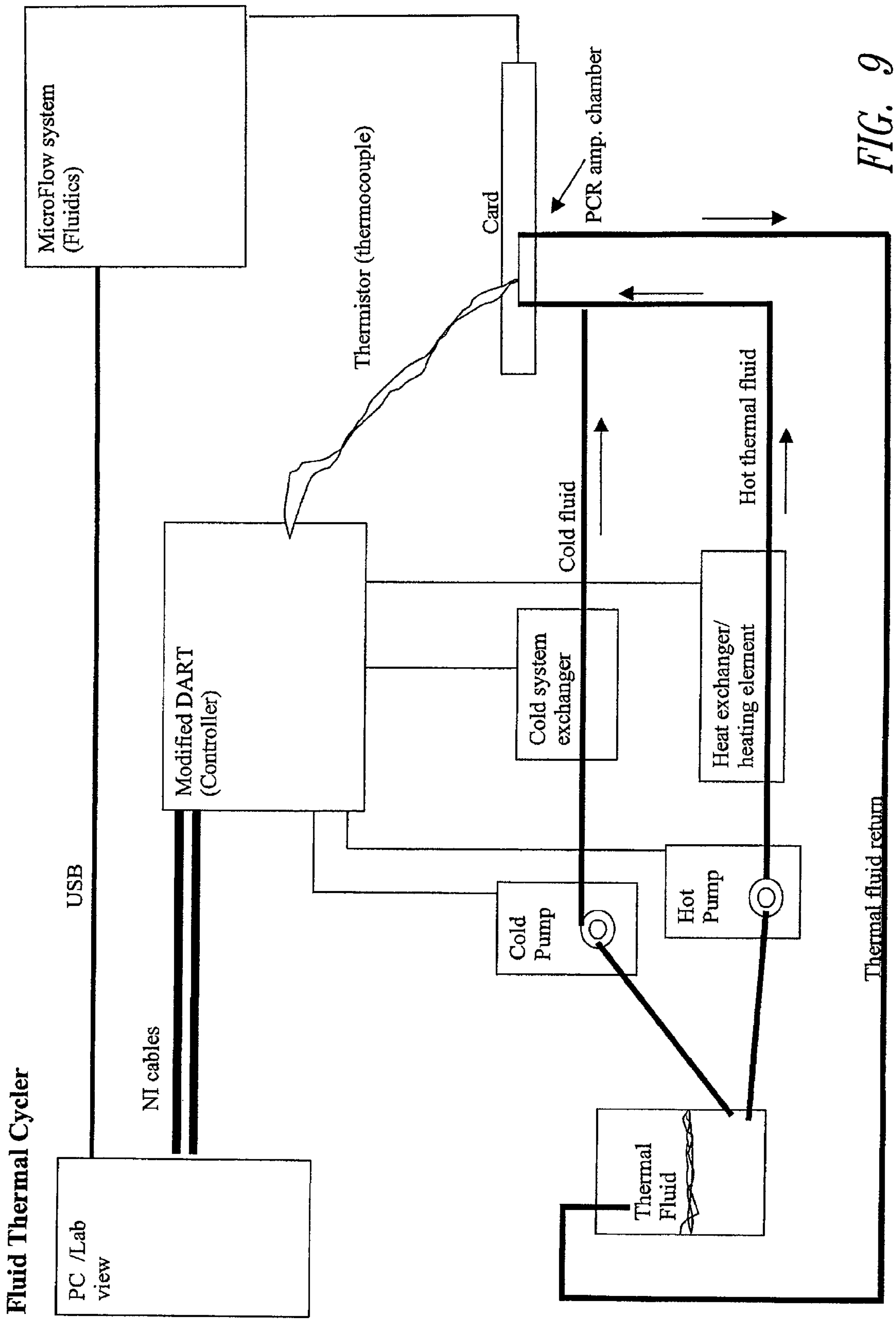
FIG. 9 is a flow chart illustrating the components of a fluid thermal cycler in accordance with principles of the present invention.

FIG. 9 is a flow chart illustrating the flow of fluid in the fluid thermal cycler described in detail above.

The thermal fluid approach to heating local areas on laminate cards has several advantages. One main advantage is the ability to locate a thermal zone for amplification in a not fixed location on the card. A second advantage is the ability to "surround" or "cover" the amplification chamber with moving thermal fluid, assuring even and rapid heating of the sample.

The system has two pumps, two heat exchangers with thermal control (hot and cold), a thermal fluid reservoir, related tubing connections, restrictors and capacitors to mitigate pulses from the pumps, a de bubbler circuit to remove bubbles created by heating a fluorocarbon thermal fluid, such as Fluorinert.

With respect to the thermal fluid, water is impractical to use as a thermal fluid because operating temperatures approach the boiling point, so Fluorinert FC-40 was tested as an alternative because of its inert properties and its relatively high boiling point of 155° C. FC-40 has a specific heat of one fourth that of water (per weight) and a thermal conductivity of about one tenth of water. FC-40 is extremely inert and volatile enough that spills and leaks evaporate readily. Those skilled in the art understand that many other thermal fluids can be used in accordance with the teachings of this invention.

Because the thermal fluid is not an efficient heat transfer material there are limits to how far from the entry port and how large the amplification chamber(s) can be. All components from the heat exchanger to the card have some thermal mass that has to be heated or cooled during thermal cycling. To accommodate a larger amplification area would require increasing flow or slowing down cycle rates.

One issue when heating the Fluorinert FC-40 to the required temperature is that any air that was dissolved in the fluid came out of solution at high temperatures. Small bubbles tended to collect at high points in the circuit. When the accumulated air created a bubble large enough to block the fluid flow it was pushed along causing problems in temperature control. Degassing was not a practical option because the thermal fluid system could not easily be isolated from the atmosphere and the circulating fluid would tend to re-absorb air. To mitigate this problem a bubble "trap" with an air bleed off circuit was designed. Fluid from the heat exchanger is pumped into the midpoint of a chamber where the exiting fluid must leave from the bottom. Above the inlet port is chamber that can collect bubbles. There is a port at the top of this chamber that is connected to a bleed tube. The bleed tube leads back to the thermal fluid reservoir. At the reservoir end of the bleed tube a restrictor reduces the flow. A short length of. 020" PEEK tubing works as a restrictor.

Thermal Cycling Using a Thermal Electric Cooler, Peltier (TEC)

Figure 10:
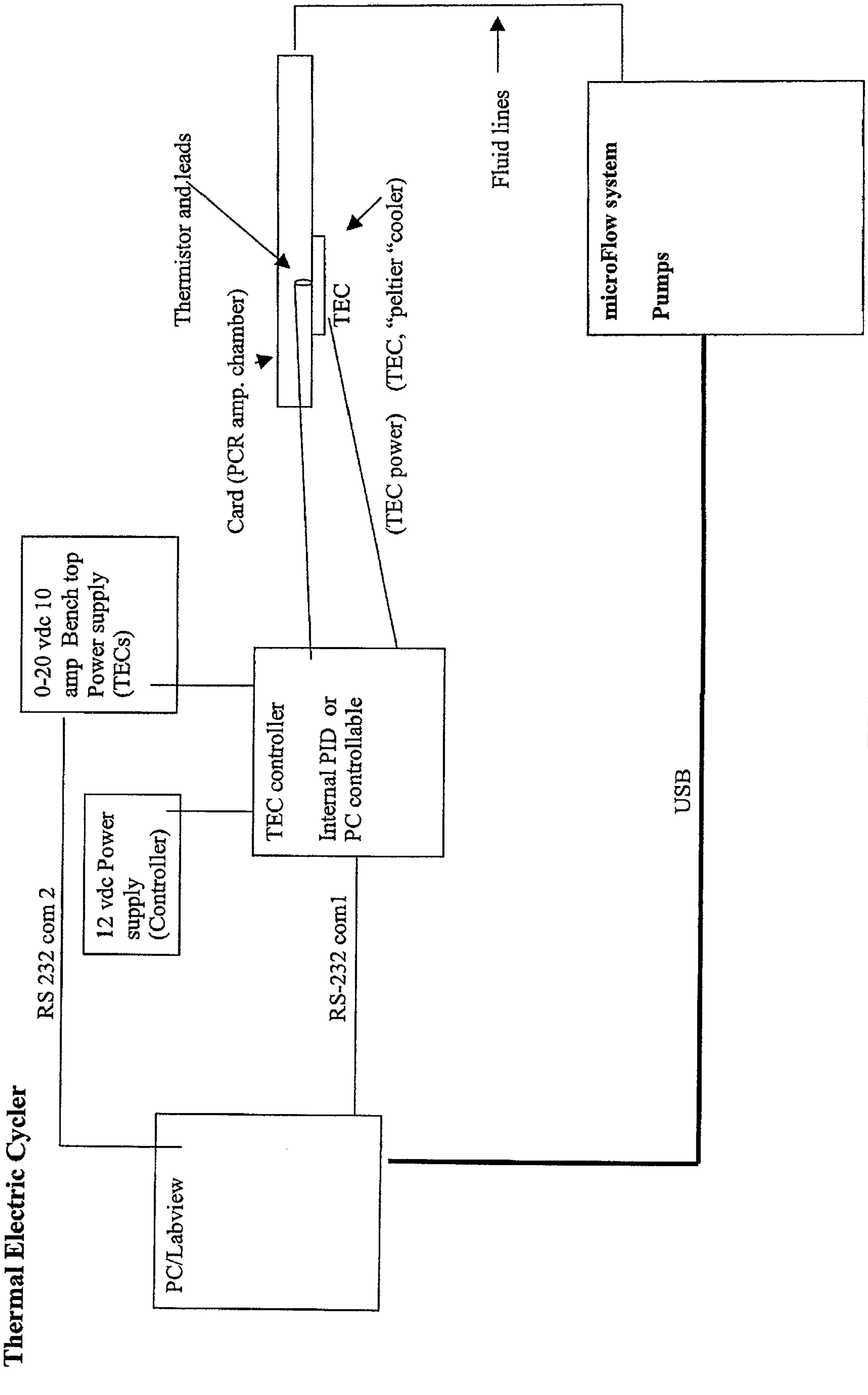
FIG. 10 is a flow chart illustrating the components of a thermal electric cycler in accordance with principles of the present invention.

In yet another alternative embodiment of the present invention, thermal cycling may be accomplished using a thermal electric cooler (TEC) such as a Peltier. FIG. 10 illustrates a flow diagram of the components of the Thermal Electric Cycler of the present invention as further described below. This configuration was used to test the feasibility of using a TEC as a heating and cooling source for microfluidic amplification chambers for use with PCR and rtPCR.

Equipment used included a Power supply 0-20 VDC (Set to 7.5 VDC); DPDT switch to reverse current direction; Heat sink; digital voltmeter; TEC (Melcor CPO-8-63-06MM, 12 mm×25 mm, Imax 2. 1A, V max 7.62 VDC); thermocouple; and Micronics "run motor" software and Thermocycler Dart, for data acquisition.

Exemplary TEC Controller Configuration:

Communication via PC

- RS-232
- USB
- GPIB

Thermistor sensors 20° C. to 100° C.

Ability to drive TEC up to temperature and down to temperature.

Current load 3.7 amps at 19VDC (optionally 7.4 amps)

Adjustable voltage output 0-20 vdc with current limits (or ability to use separate power supply)

Ability to poll and collect data.

Fast PID loop (P=1° C. to 200° C., I=1 sec or less, D=1 sec or less)

Ability to use different PID loop for heating and cooling.

Ramp and soak to three temperatures minimum. Ramp rate 6° C. per second or faster.

One exemplary target profile: Heat to 65-75° C. and hold for 60 seconds. Ramp as quickly as possible to 94-95° C., hold (soak) for 5 seconds; ramp down to 65-70° C., hold (soak) for another 5 seconds. Repeat previous two steps (94 and 72° C.). Total number of repeats estimated at 40 each.

Temperature and soak times are based on the chemistry chosen for the amplification.

A second exemplary target profile: 95° C. for 3 minutes, 27° C. for 30 sec, 65° C. for 10 minutes. There is another 5 step variation of this with temperatures from 27 to 95 with varying times. But it illustrates the PID requirements.

A third exemplary target profile: hold a temperature for up to 90 minutes.

Test setup and results: In all tests the TEC was operated at 7.5 V.

Test Operation:

A TEC was placed on a stainless steel table to act as a heat sink. A thermocouple was taped to the top surface of the TEC. Data was taken as the TEC was cycled from hot to cold. This test yielded data that showed a transition time of 4.25 seconds to go from 60° C. to 95° C. or 8.65° C./sec. Cool down time was 3 seconds to go from 96° C. to 60° C. or 12° C./sec.

This test proved the feasibility of changing the temperature using a TEC.

Amplification chamber tests:

A simple laminate card was designed with an amplification chamber capped by one layer of 0.004"Mylar® (polyethylene terephthalate).

Figure 29:
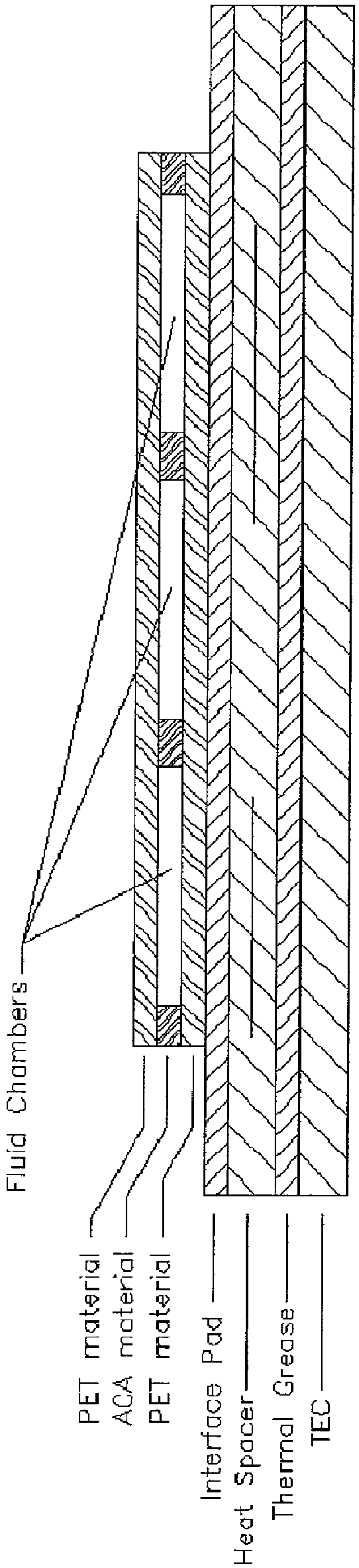
FIG. 29 is a cross section of a microfluidic card using a TEC for thermocycling in accordance with principles of the present invention.

As shown in FIG. 3 and FIG. 29, the Mylar layer is sealed in place with a double-sided ACA adhesive layer. Mylar has good transparency and can be used in devices where optical readout is desired. Also preferred for their transparency in the visual and UV spectrum in applications where fluorometric detection is required are cyclic polyolefins such as Topas® (Ticona Corp, Florence Ky.) and Zenor® (Zeon Chemicals, Tokyo JP). Both the thermoplastic and the ACA (adhesive-carrier-adhesive) film layers can be supplied as sheet stock or as roll stock for manual or continuous lamination assembly. Optionally, roll stock is fed into an automated continuous assembler; the advantage of roll stock of Mylar and ACA films being that a "kiss" laser cut can be performed on the ACA film prior to assembly and unwanted cutouts of the adhesive film removed with the first release layer, thereby ensuring that heat transfer across the Mylar layer is unimpeded by the presence of a glue layer in areas where adhesive is not needed. The cutouts generally conform to the outline of the amplification chambers so that the amplification chambers are not capped by the ACA layer. ACA roll stock is typically supplied as a 5-layer substrate, the outermost top and bottom release layers of which are removed from the underlying pressure sensitive adhesive layers and central core layer immediately before assembly. Individual laminated cards may also be manufactured manually from roll or sheet stock.

Figure 11:
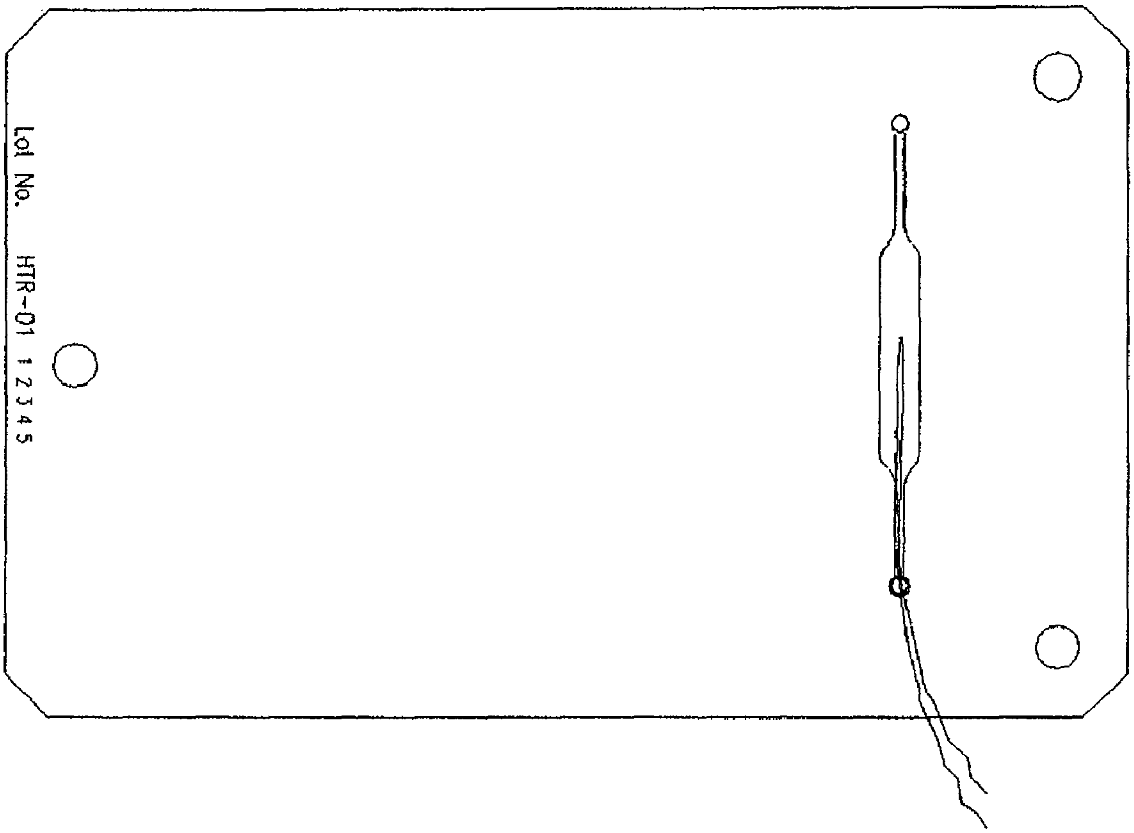
FIG. 11 is a schematic of a microfluidic test laminate with a thermocouple inserted into the amplification chamber in accordance with principles of the present invention.

This allows the polyethylene terephthalate capping layer of the chamber to be placed in direct contact with the TEC. As shown in FIG. 11, a thermocouple was inserted into the amplification chamber and the chamber was filled with Fluorinert FC-40.

The designed volume of the amplification chamber is approximately 10 uL. This is increased slightly because the thermocouple causes a bulge in the chamber. Actual volume is estimated between 15 and 20 uL. The thermocouple monitors the temperature of the amplification chamber.

The first test was with the laminate placed directly against the TEC. An insulating pad was placed over the laminate and a 3.5 oz weight placed on top to provide some pressure.

Figure 12:
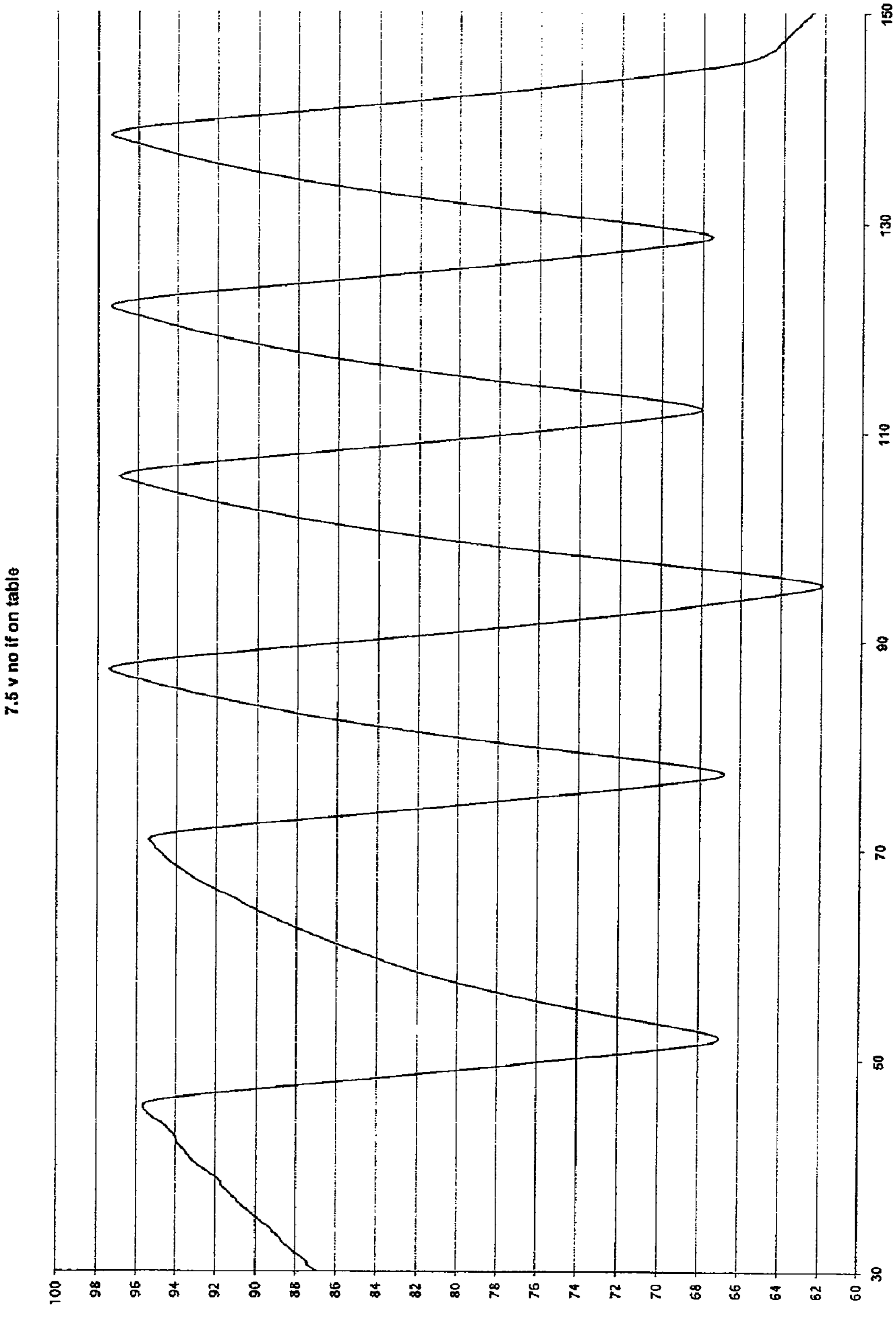
FIG. 12 is a graph illustrating temperature variation over time when a TEC is placed directly 9 on a stainless steel table with no thermal interface material between the TEC and the microfluidic card in accordance with principles of the present invention.
Figure 13:
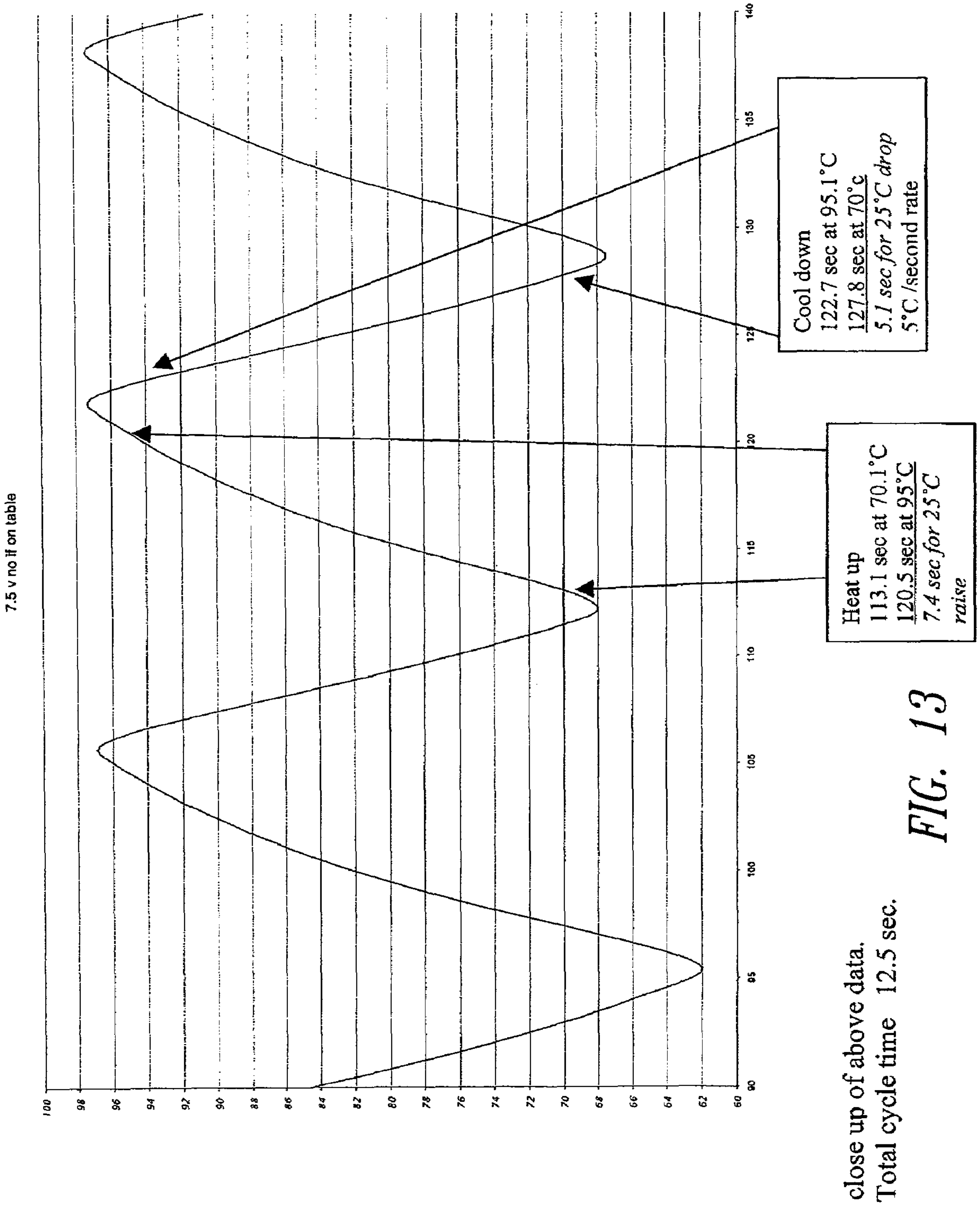
FIG. 13 is a graph illustrating temperature variation overtime when a TEC is placed on a heat sink and a layer of graphite thermal interface pad is placed between the TEC and the laminate in accordance with principles of the present invention.

In the chart of FIG. 12, at 7.5V, using no interface material, and TEC directly on table, it can be seen that the heat-up is slower then the cool down; especially at first. FIG. 13 illustrates a close-up of some of the data in FIG. 12.

Figure 14:
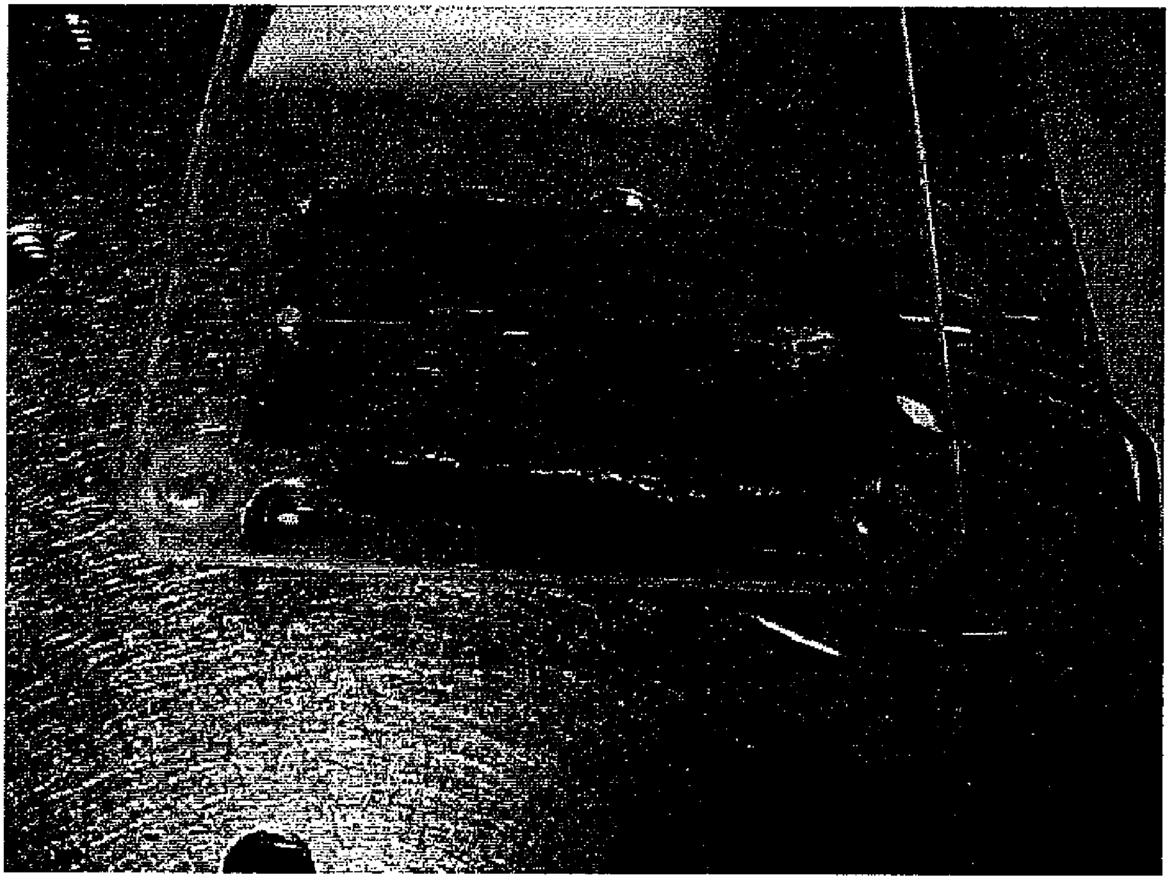
FIG. 14 is a photograph of the card of FIG. 13 in accordance with principles of the present invention.

A second test was performed. This time the TEC was placed on a heat sink and a layer of graphite thermal interface pad was placed between the TEC and the laminate. FIG. 13 illustrates a card on TEC with heat sink and graphite pad. FIG. 14 is a photograph of the card tested yielding the results in FIG. 13.

Figure 15:
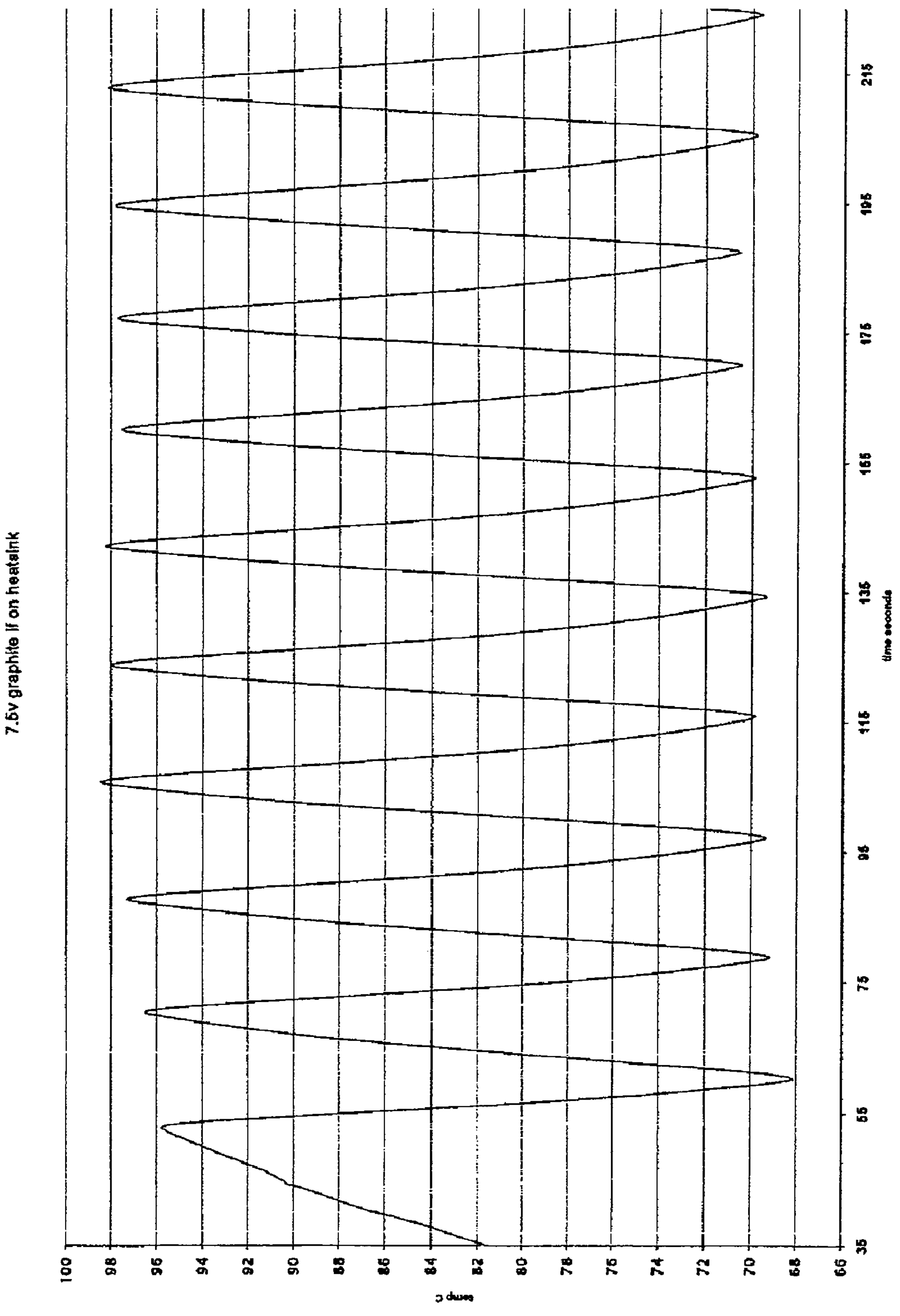
FIG. 15 is a graph illustrating temperature variation over time when a TEC is placed on a heat sink and a graphite pad between the TEC and amplification chamber in accordance with principles of the present invention.
Figure 16:
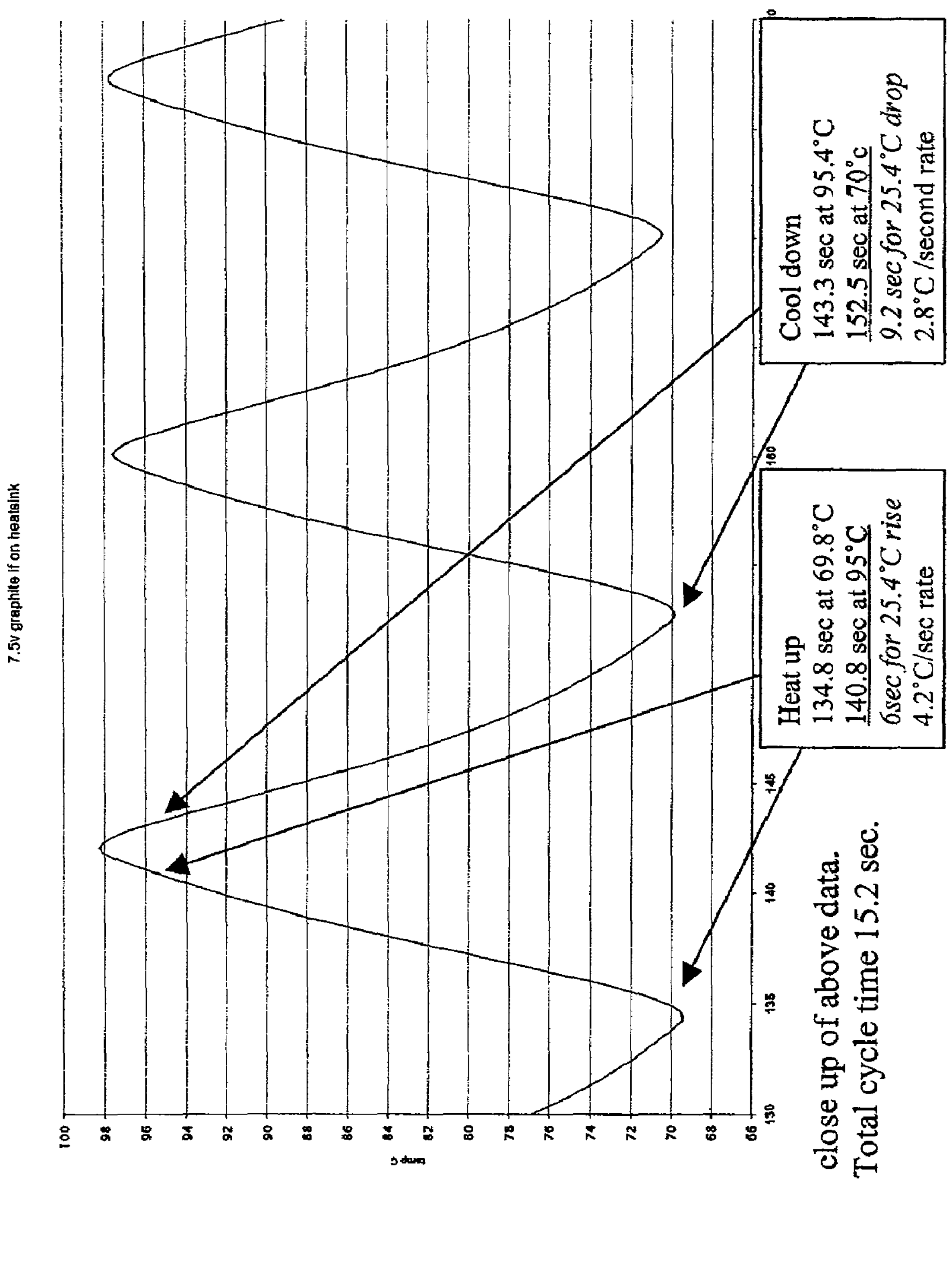
FIG. 16 is a close up of a portion of the graph of FIG. 15.

FIG. 15 illustrates a TEC on a heat sink and a graphite pad between the TEC and Amplification chamber. Note that in the first figure, the heat up is more constant without the rate tapering off at the end (after the initial heat up). The cool down rate however does taper off. FIG. 16 illustrates a close up of the above data. The total cycle time was 15.2 seconds.

Comments:

A TEC moves heat from one side to the other; in the process it adds heat (TECs draw quite a bit of current). If the cold side is against an already cold surface the heat transferred from that surface is minimal and the heating that takes place on the "hot" side is primarily from the electrical current passing through the TEC. This is evident in the first test where the TEC was directly in contact with a cool stainless steel table (around 17° C.). After several cycles the area under the TEC heats up slightly and the rise time from 70 to 95° C. is quicker.

Cool down time is rapid because there is enough temperature differential between the TEC and the table to move the heat away quickly.

When the TEC is mounted on the heat sink, the heat sink is able to store heat that can be transferred quickly to the laminate. Thus the rise time is quicker. However the cool down time is longer because the temperature differential between the TEC and the sink can't carry away the excess heat very quickly.

The above illustrates a thermal balance that must be achieved for efficient (and consistent) operation. The heat sink should have enough heat stored to transfer quickly to the laminate at the same time it should not be so hot that it slows down the cooling process.

The graphite thermal interface material used is the only material tested, other suitable materials may be used.

The TEC used in these tests was a relatively inexpensive and inefficient one. Higher power TECs are readily available. The maximum temperature difference between hot and cold side is around 60° C. without cascading. In the present embodiment, we also consider using a cascaded (stacked) TEC. Some applications may need a 27° C. to 95° C. range. A cascaded TEC moves the heat to and from the card and prevents a heat buildup.

CONCLUSIONS

The cycle time of 16 seconds (worst case in tests) can be improved on greatly with proper sized heat sinks, TECs, and more efficient thermal interface material. Even at 16 seconds 30 full cycles will only take 8 minutes. The TEC is sized to match the amplifier area of the card.

Updated Testing:

The above cycle tests were repeated using Parker Chomerics Thermagap material 61-02-0404-F574. (0.020" thick). The 574 series is a soft elastomer (<5 Shore A) needing only a pressure of 5 to 10 psi to provide a thermal conductivity of 1.6 W/m-K.

Figure 17:
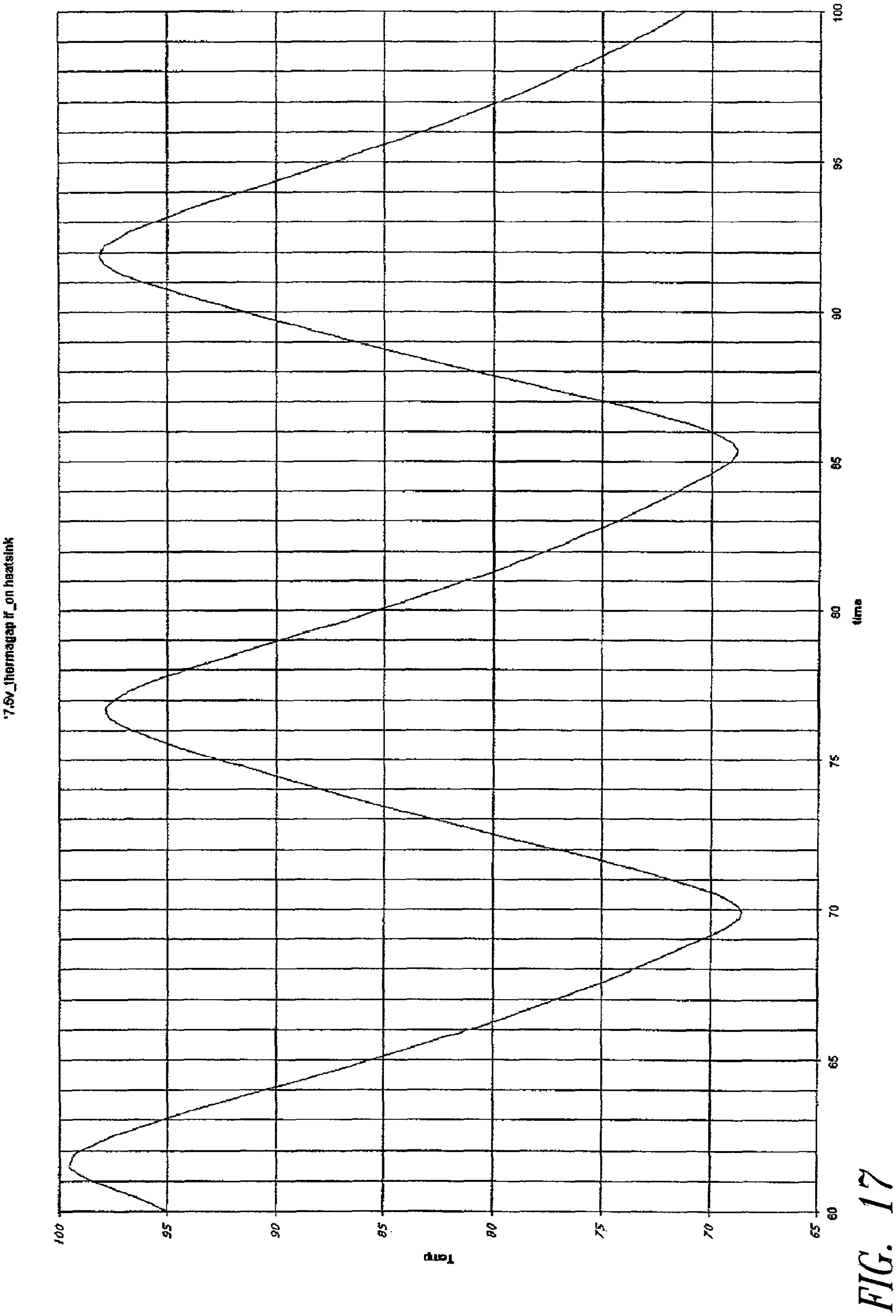
FIG. 17 is a graph illustrating temperature variation over time when a TEC is placed on a Thermagap heat sink in accordance with principles of the present invention.

The timing for a full cycle was 13 about 14 seconds including a one second turn around time at top and bottom of the cycle. Thirty complete cycles would take 7 minutes. Rise rate 55° C./sec. Fall rate-4° C./sec. See the following graph shown in FIG. 17. Note that the ramp up and ramp down require a "rounding off" at the target temperature to avoid overshoot. This can increase the overall cycle time significantly. A tight PID control loop can minimize this round off.

Thermal Cycler Graphic Interface (GUI)

Figure 18:
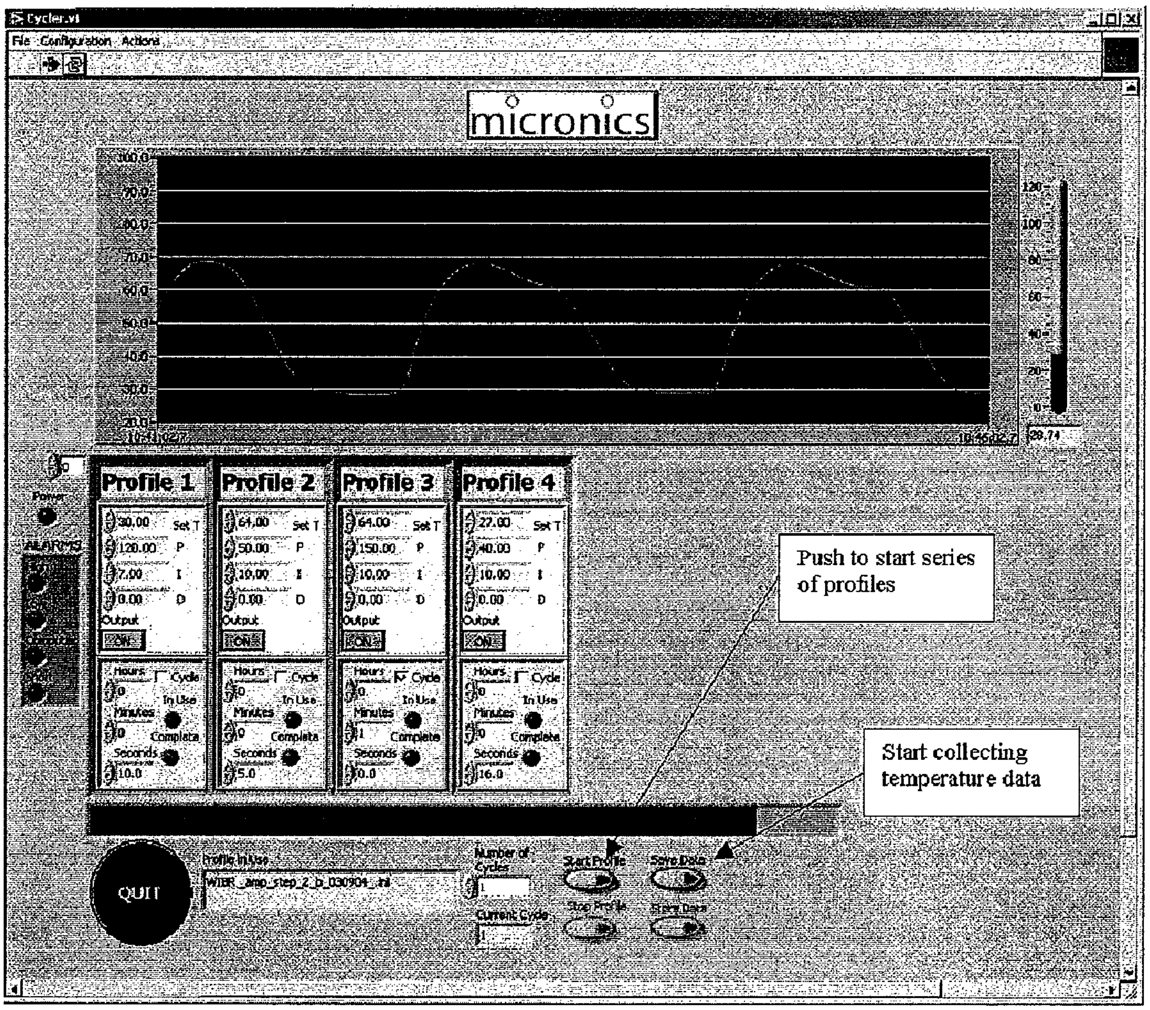
FIG. 18 is a screenshot of a Thermal Cycler Graphic Interface (GUI) in accordance with principles of the present invention.

As shown in FIG. 18, the Thermal Cycler Graphic Interface allows the Scientist or Technician to develop and tune thermal profiles for assay development. Custom profiles can be developed for different heating and cooling requirements.

Figure 19:
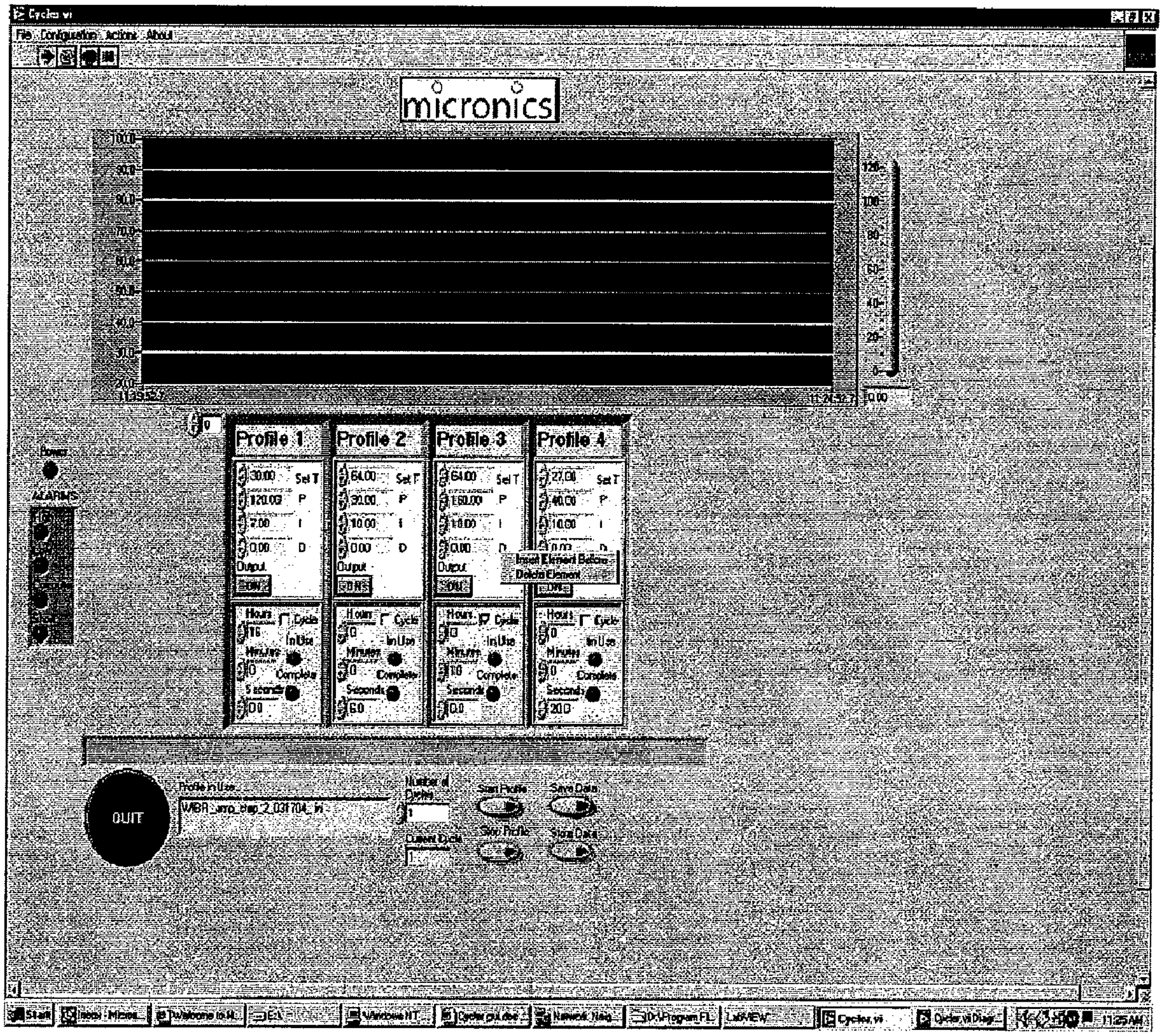
FIG. 19 is a screenshot of the GUI illustrating the addition or deletion of a Profile in accordance with principles of the present invention.

In FIG. 19, the Graph depicts the temperature at the Control Thermistor. The PID loop (Proportional Integral and Derivative) can be adjusted in the top panel to tune each profile. Timing can be set in the lower panel of each Profile. Data can be recorded by pressing the "Save Data" button. Press the "Store Data" Button when you want to stop saving. Save as a CSV file.

As shown in FIG. 19, adding or deleting a Profile (element) in a series can be done by right clicking the PID panel near the D or P. Select insert or delete.

Figure 20:
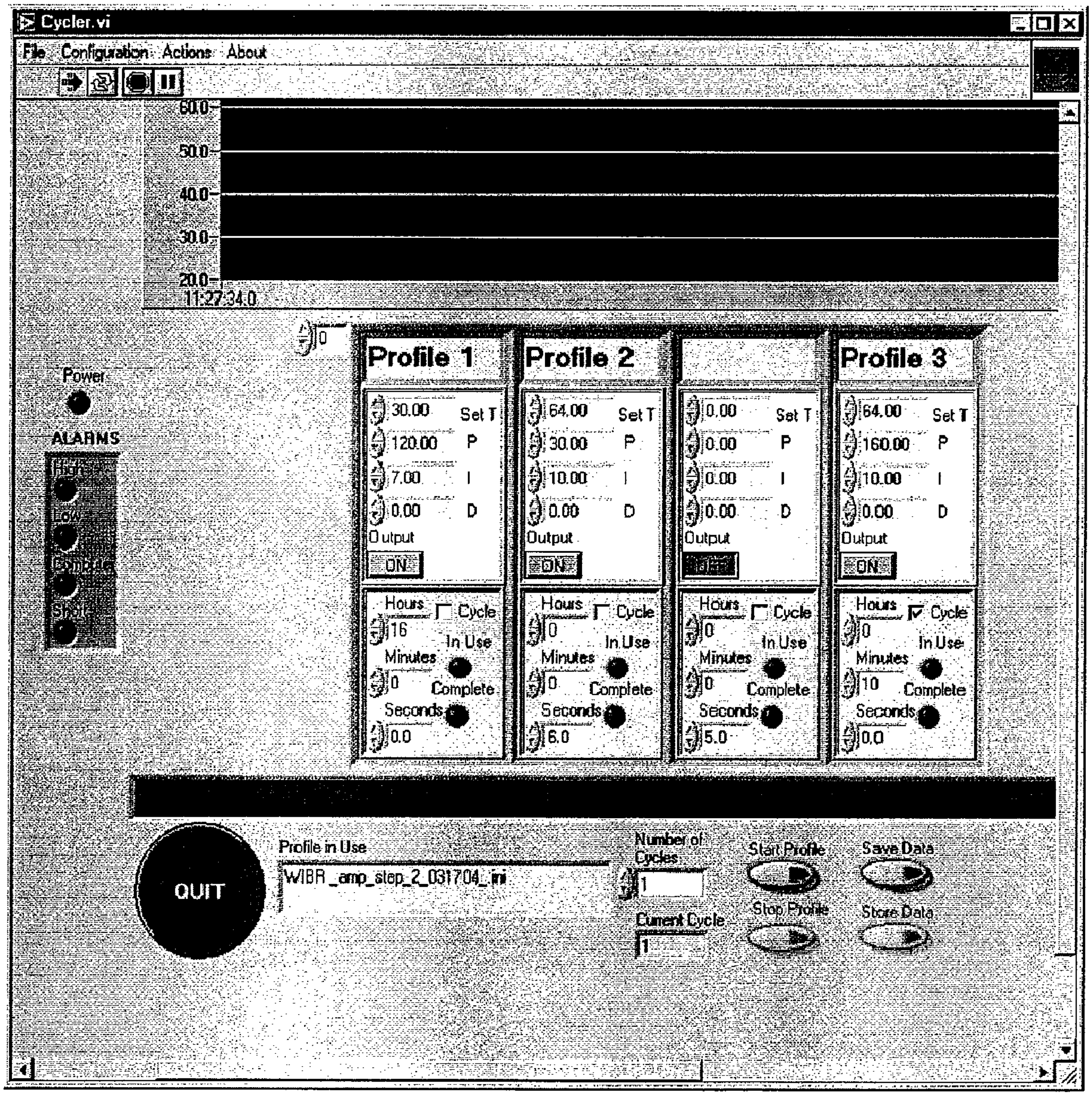
FIG. 20 is another screenshot of the GUI in accordance with principles of the present invention.

As shown in FIG. 20, the new element is inserted between Profiles 2 and 3. In this case we are including a 5 second "Profile" where the temperature controller is turned "OFF". When tuning a series of profiles it is sometimes advantageous to turn the TEC off for a few seconds. This can be particularly helpful when cooling down to avoid overshooting.

Figure 21:
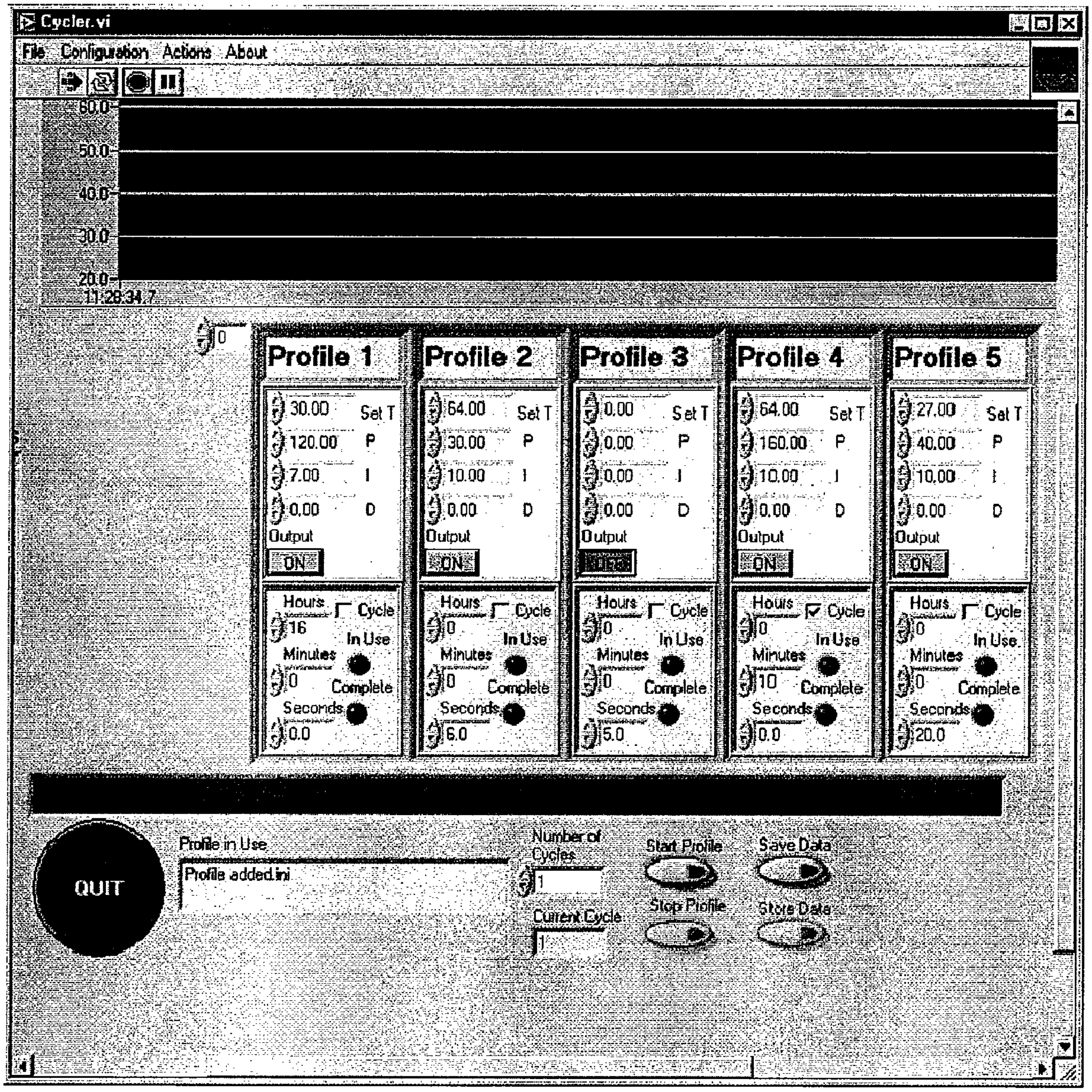
FIG. 21 is another screenshot of the GUI in accordance with principles of the present invention.

As shown in FIG. 21, after saving, the new Profile becomes Profile 3 and the original Profile 3 becomes Profile 4.

Figure 22:
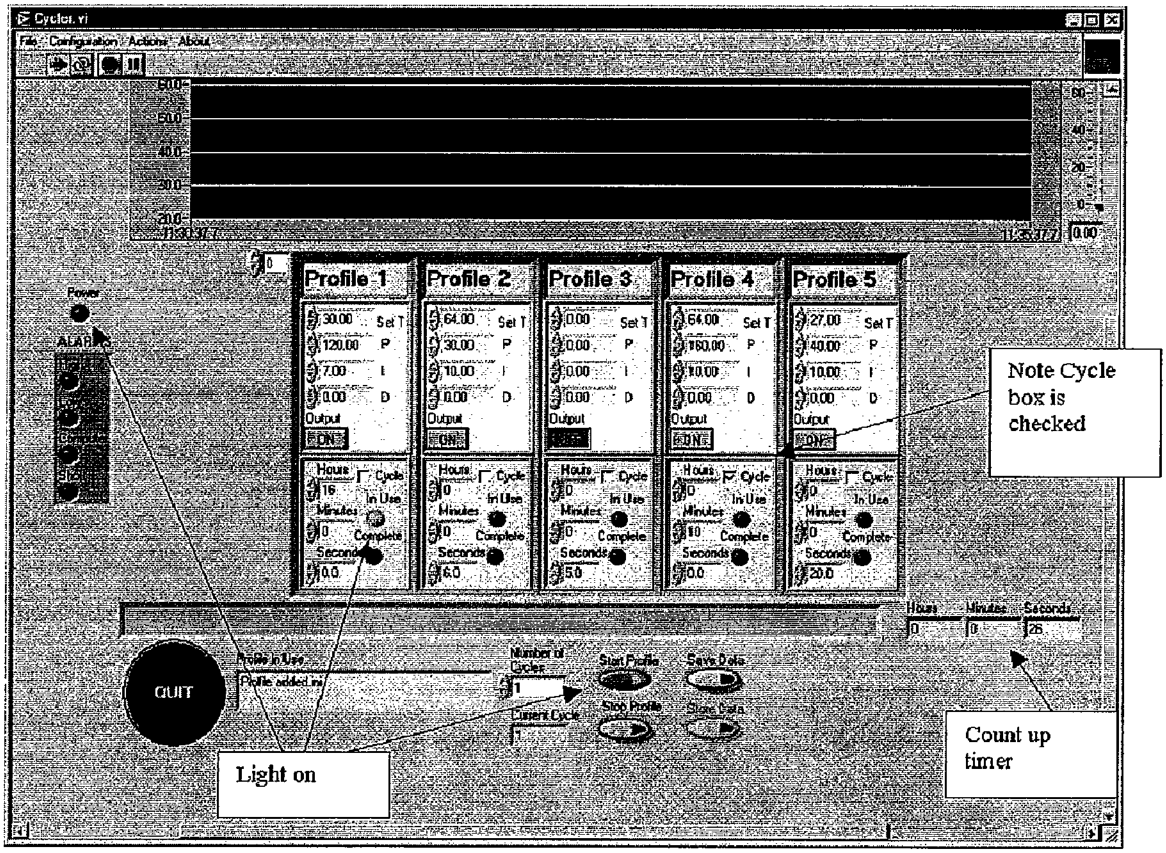
FIG. 22 is another screenshot of the GUI in accordance with principles of the present invention.

As illustrated in FIG. 22, a series has been started. The Start Profile light is lit. The In Use light indicates which profile is active. (The Power light would also be lit if this was not from a simulation.) The Count timer displays how long the Profile has been active. The number of Cycles to be performed is selected in the "Number of Cycles" box. Note that All Profile series must have at least one box checked indicating it is to be cycled. By indicating 1 cycle in the "Number of Cycles" box the Entire series can be run from start to finish without any repeats. A long series of Profiles to cycle can be strung together. Individual not repeated Profiles can be placed before and after the cycled series.

Figure 23:
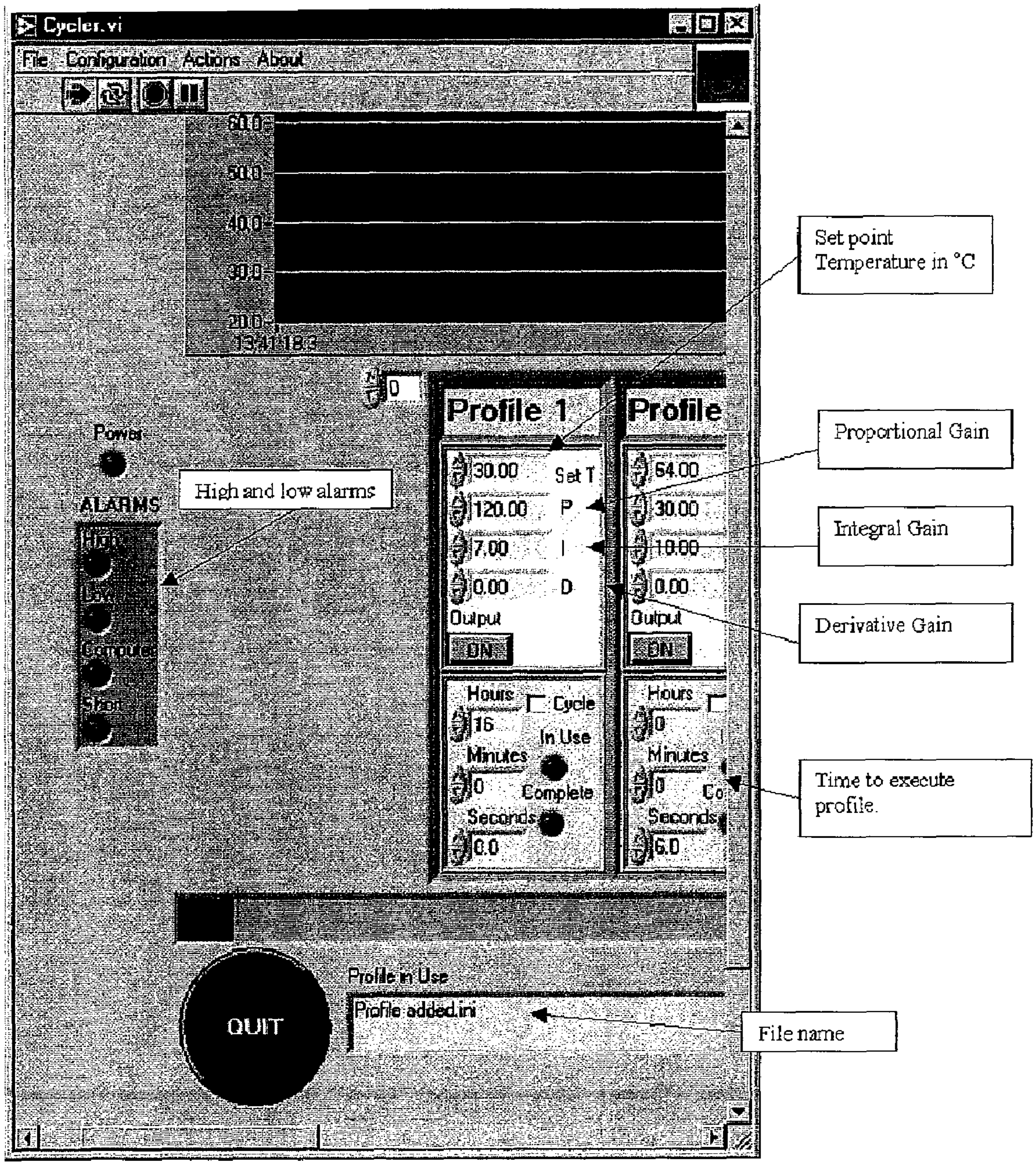
FIG. 23 is another screenshot of the GUI in accordance with principles of the present invention.

As shown in FIG. 23, there is a second thermistor mounted on the top surface of the TEC. This is monitored to guard against the overheating or cooling of the TEC. It is important to always have the control thermistor in place when running the Cycler.

Figure 24:
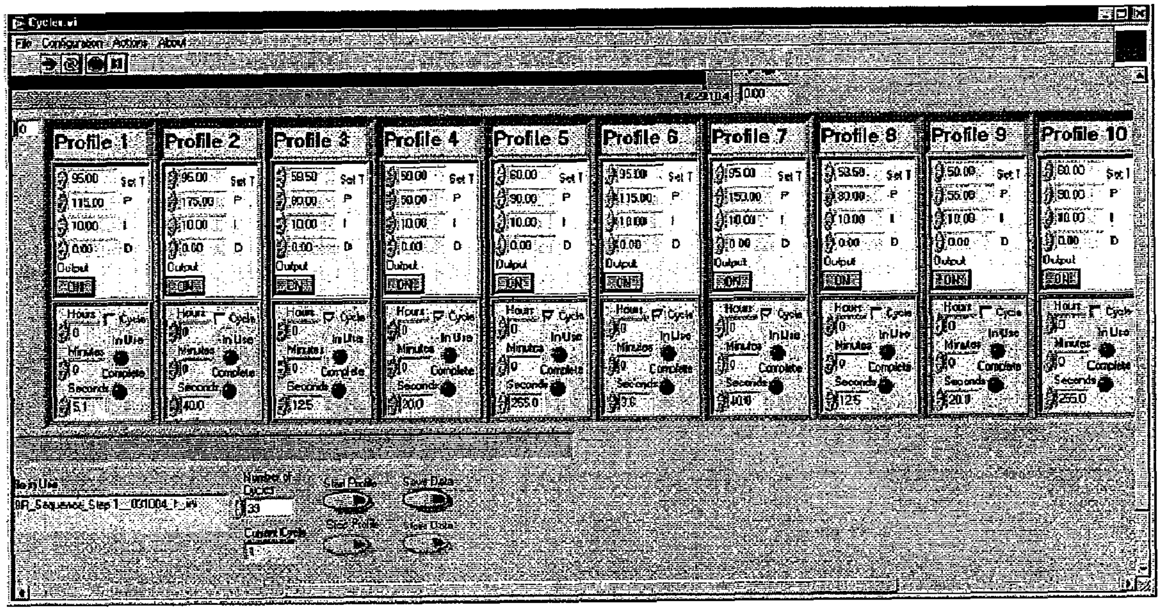
FIG. 24 is another screenshot of the GUI in accordance with principles of the present invention.

FIG. 24 illustrates an example of a long series. Profiles 1 and 2 will be performed once. Profiles 3 through 7 all have the Cycle box checked. They will be performed one after another, and then repeated 39 times (Number of Cycles=39). After Profile 7 has been performed the 39th time, Profiles 8 through 10 will be performed once. After Profile 10 is performed, the program will turn off the controller output to the TEC.

Figure 25:
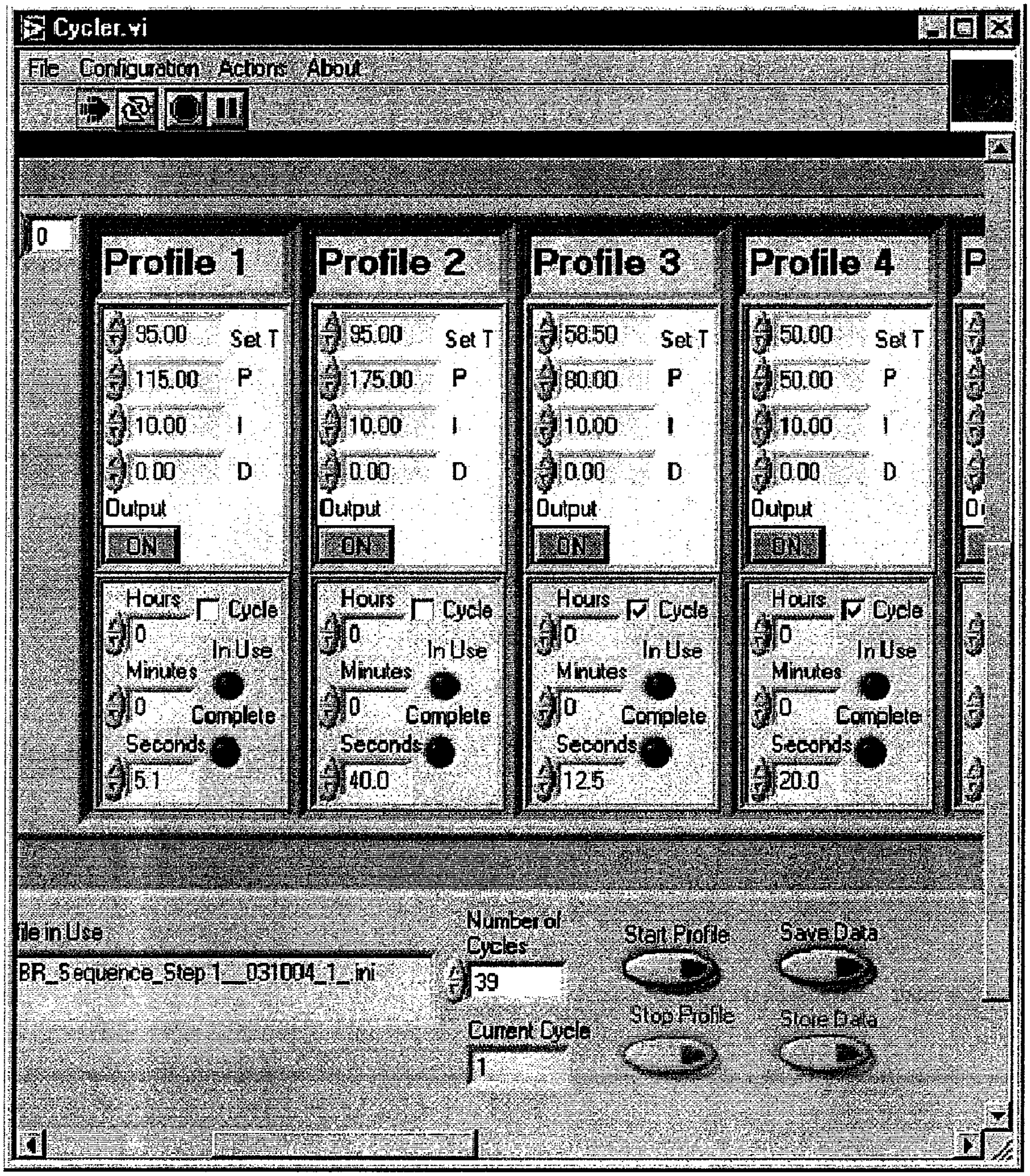
FIG. 25 is another screenshot of the GUI in accordance with principles of the present invention.

FIG. 25 illustrates an example of using two Profiles to reach a temperature with a minimum of overshoot. A lower P (Proportional gain) causes the controller to drive the TEC quickly. Then switching to a higher P the controller output is lowered and the temperature does not overshoot the target. In Profiles 3 and 4, the TEC is driven down to 58.5° C. Because of latency in the system it will overshoot and reverse the temperature in the TEC. The heat going into the TEC will reduce the overshoot. By adjusting the Set Temperature, Proportional gain, and timing it is possible to get the temperature to level out at the desired temperature without overshooting. Then the Profile to hold that temperature is invoked. Note that unless the output is turned off (see above) the controller will be trying to drive the TEC either up or down to the set temperature. Given enough time this will level out to a "flat line" but for rapid thermal cycling it is helpful to Tune the ramp up and down.

Figure 26:
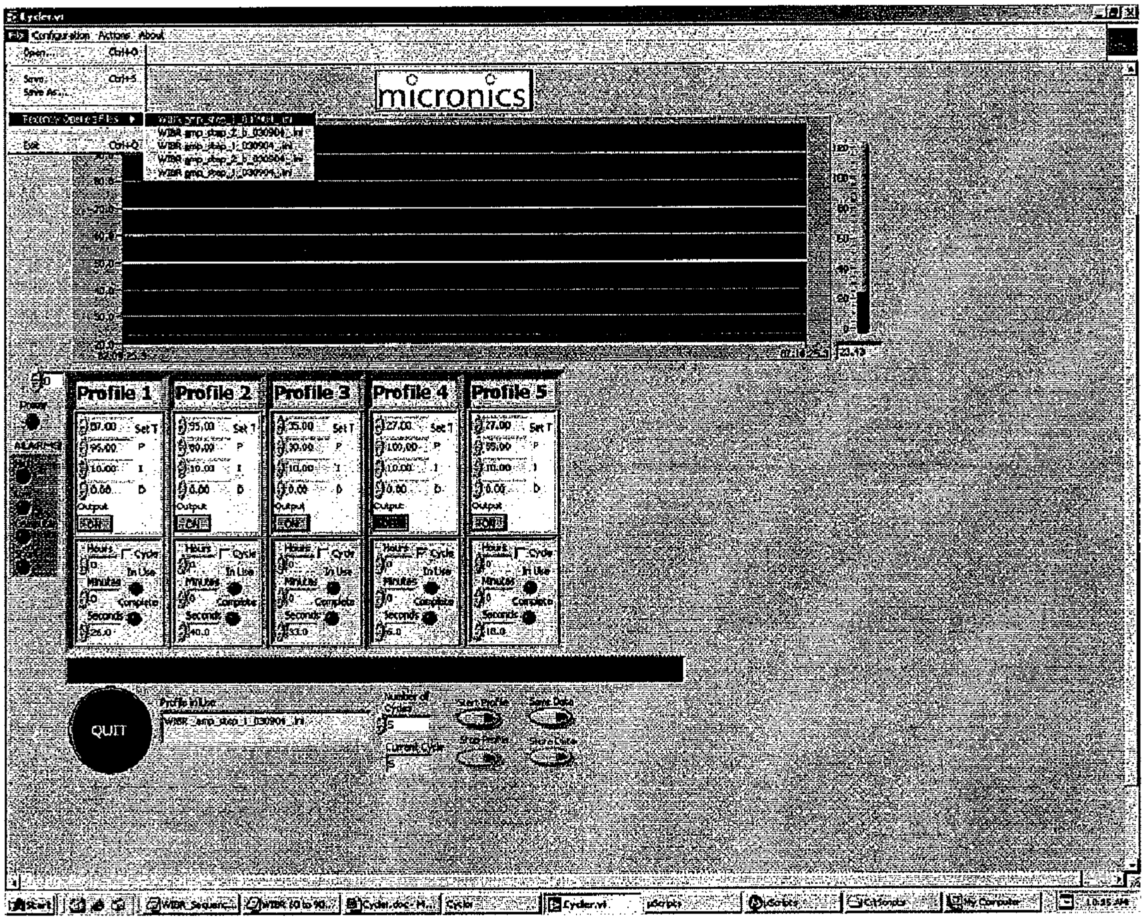
FIG. 26 is another screenshot of the GUI in accordance with principles of the present invention.
Figure 27:
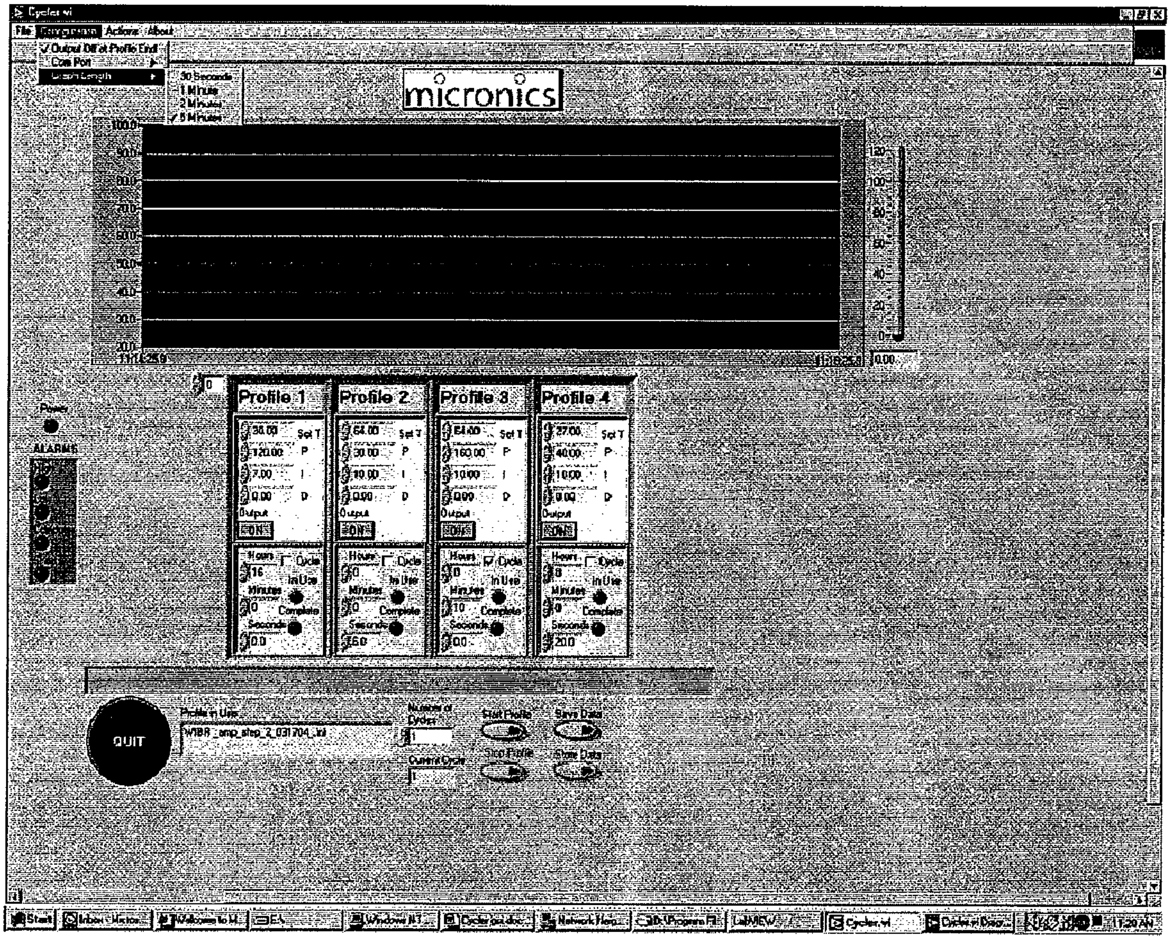
FIG. 27 is another screenshot of the GUI in accordance with principles of the present invention.
Figure 28:
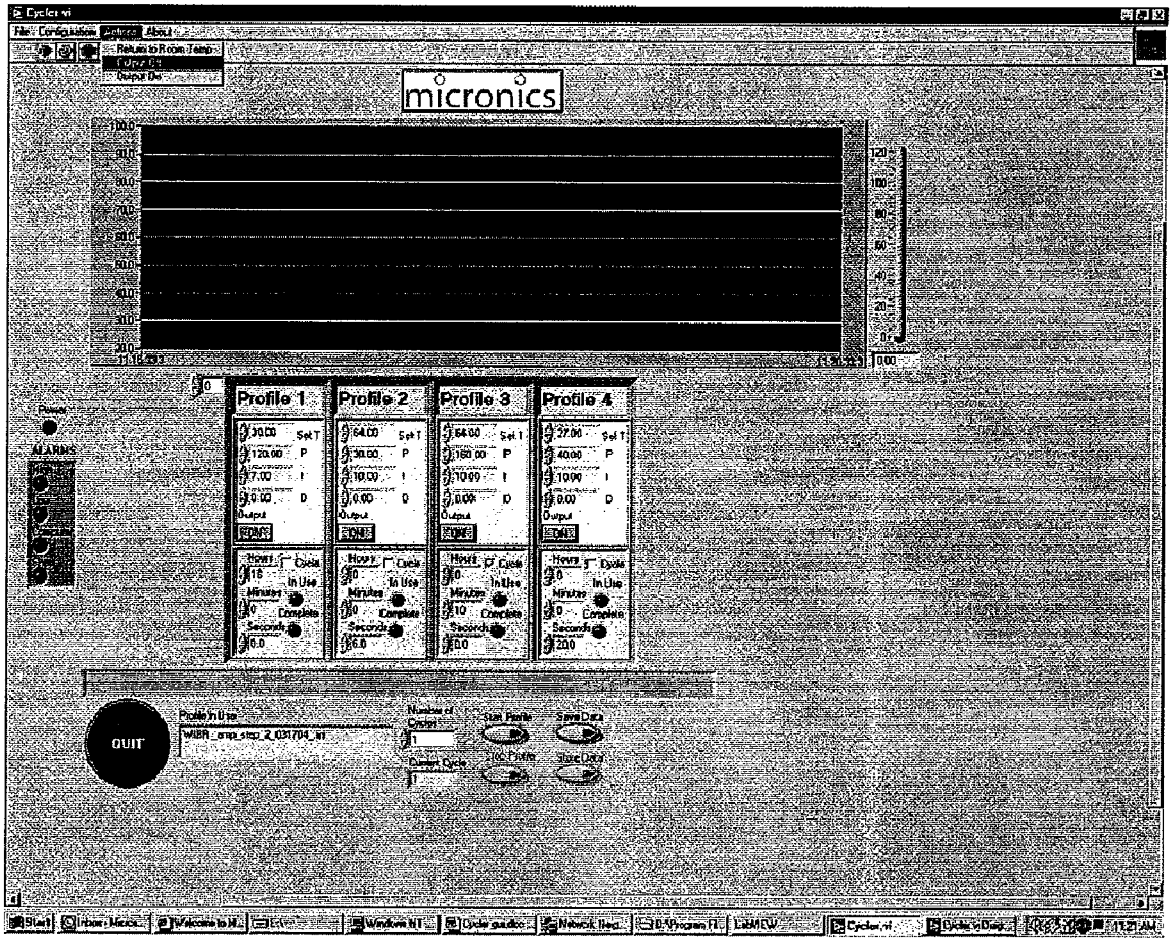
FIG. 28 is another screenshot of the GUI in accordance with principles of the present invention.

FIGS. 26 through 28 illustrate various aspects of the GUI. Using the pull down menu the last Opened files can be selected. The displayed graph time can be selected from 30 seconds to 5 minutes. "Room temperature" can be selected, as well as output on or off. Note the controller output is turned off after a series is completed. It is often helpful to have a room temperature Profile at the end of a series. When the controller is turned on it drives the TEC to the last "Set temperature."

FIG. 29 is a cross section of a microfluidic card using a TEC for thermocycling in accordance with principles of the present invention as discussed above. In FIG. 29, multiple amplification reservoirs or fluid chambers are simultaneously cycled by the TEC. The amplification reservoirs are contained between layers of PET material and an ACA (adhesive-carrier-adhesive) material to provide a disposable microfluidic card.

As further illustrated in FIG. 29, a heat spacer or heat spreader may be used between the TEC and the amplification reservoirs in order to provide a more uniform heat across the TEC surface. The heat spreader will ultimately be determined by the thermal profile of the TEC, but one exemplary heat spreader is a layer of PTFE between layers of copper, however those skilled in the art will understand that many variations of heat spreaders are acceptable.

The interface pad illustrated in FIG. 29 is a thermal pad to more efficiently transfer heat to the microfluidic card. Likewise, the thermal grease between the TEC and the heat spreader or spacer is know to those in the art to further enhance heat transfer.

Exemplary Amplification Methods and Temperature Cycles

The following temperature profiles have been achieved on microfluidic cards using methods and apparatuses of the present invention.

Figure 30A:
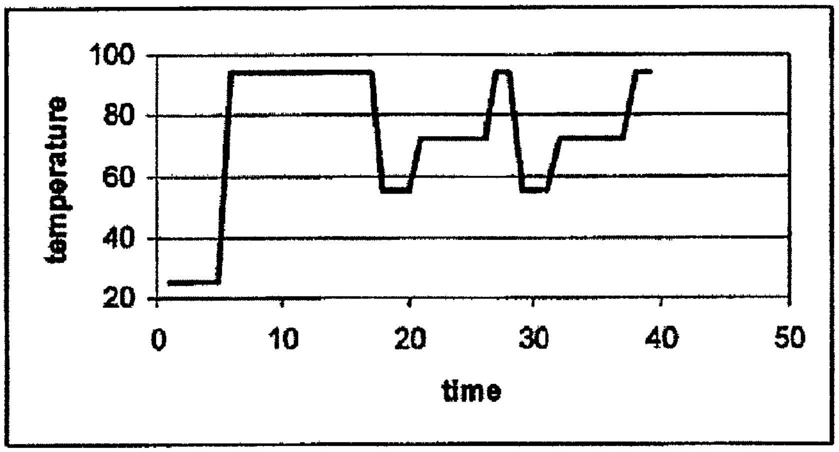
FIG. 30A-D are temperature profiles achieved on microfluidic cards of the present invention. Shown are a PCR profile, NASBA profile, reverse transcription profile, and LAMP profile.

FIG. 30A shows a Polymerase Chain Reaction (PCR) Temperature Profile. The profile demonstrates: 1) Consistent; 2) Adjustable and accurate temperature for anneal step (lowest T); 3) Adjustable hold time for anneal step; 4) Adjustable hold time at extension step (72° C.); 5) Do not exceed 95° C. (prevents denaturing of enzyme), and 6) Rapid cycling.

Figure 30B:
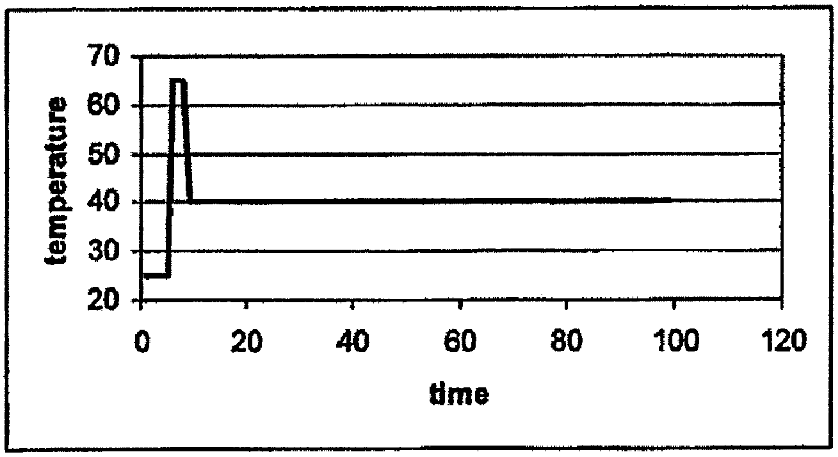

FIG. 30B shows a Nucleic Acid Sequence Based Analysis (NASBA) Temperature Profile. The profile demonstrates: 1) Stable 40 +/−1.0° C. temperature (>42° C. denatures enzyme); 2) Adjustable hold times for 65° C. and 40° C., with 90 minutes maximum for 40° C.; 3) 65° C. or greater is OK; 4) 2 to 5 minute hold at 65° C. is standard, but shorter may be OK; 5) Consistent time to 40° C. after 65° C. (for programmed enzyme addition), and 6) Shorter is better, but 1-2 minutes for cooling from 65 to 40° C. is OK. Current block heaters used with DART take-10 minutes-current thermal cyclers take about 1 minute to cool.

Figure 30C:
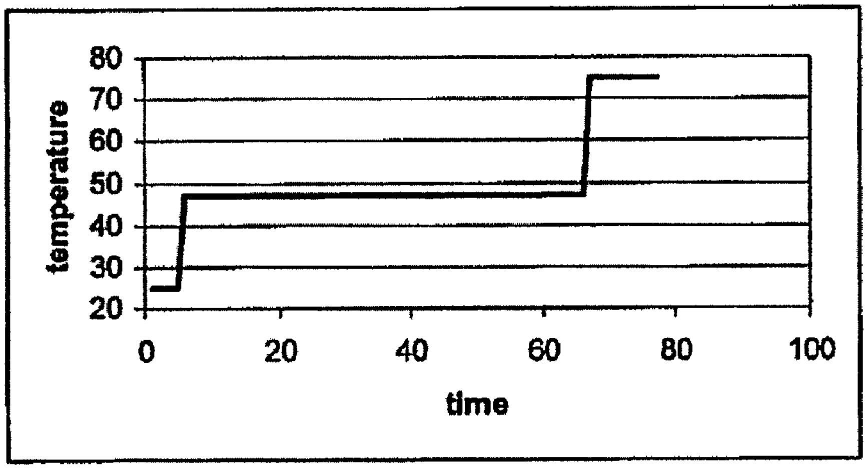

FIG. 30C shows a Reverse Transcriptase (rt) Temperature Profile. The profile demonstrates: 1) Stable 47° C. temperature with zero or minimal overshoot; 2) Adjustable hold time for 47° C., with 60 min maximum, and 3) Rapid rise to 75° C. or higher for 10 minutes.

Figure 30D:
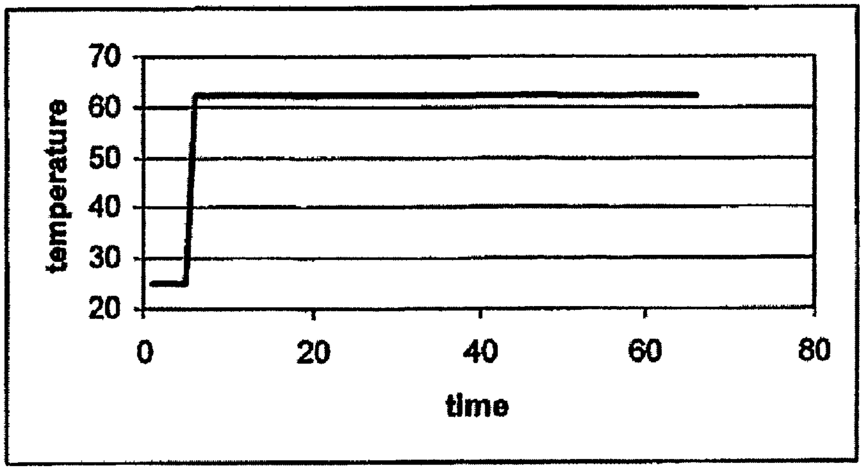

FIG. 30D shows a Loop Mediated Amplification (LAMP) Temperature Profile. The profile demonstrates: 1) Stable 62° C. with minimal overshoot, and 2) Adjustable hold time for 62° C., with 60 minutes maximum.

The above description of illustrated embodiments of the invention is not intended to be exhaustive or to limit the invention to the precise form discloses. While specific embodiments of, and examples for, the invention are described herein for illustrative purposes, various equivalent modifications are possible within the scope of the invention, as those skilled in the relevant art will recognize. The teachings provided herein of the invention can be applied to other microfluidic devices, not necessarily the PCR and rtPCR cards described above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A microfluidic device for amplifying a nucleic acid comprising:

a) a first plate with a first surface and a second surface;

b) a first amplification chamber formed in said first surface;

c) a microfluidic assay fluid circuit fluidly connected to said first amplification chamber; and d) a heat exchange film covering and sealing over said first amplification chamber, said heat exchange film with interior surface facing said first surface of said first plate and with oppositely facing exterior surface, wherein said interior surface of said heat exchange film is an optically transparent polyethylene terephthalate roll stock film.

2. The microfluidic device of claim 1 wherein said optically transparent polyethylene terephthalate roll stock film has a thickness of less than or equal to 0.004 inches.

3. The microfluidic device of claim 1 wherein said optically transparent polyethylene terephthalate roll stock film has a thickness of less than or equal to 0.002 inches.

4. The thermocycling apparatus of claim 1 wherein said heat exchange film is sealed to said first surface with a double-sided ACA adhesive layer.

5. The microfluidic device of claim 1, wherein said device is configured for performing an enzymatic reaction selected from the group consisting of PCR, NASBA, reverse transcription, and LAMP.

6. A microfluidic device for amplifying a nucleic acid comprising:

a) a first plate with a first surface and a second surface;

b) a first amplification chamber formed in said first surface;

c) a microfluidic assay fluid circuit fluidly connected to said first amplification chamber; and d) a heat exchange film covering and sealing over said first amplification chamber, said heat exchange film with interior surface facing said first surface of said first plate and with oppositely facing exterior surface, wherein said interior surface of said heat exchange film is an optically transparent polyethylene terephthalate roll stock film, and wherein said heat-exchange film is joined to said first plate by a double sided ACA adhesive layer with laser cutout to seal around but not cover said amplification chambers.

7. The microfluidic device of claim 6, wherein said device is configured for performing an enzymatic reaction selected from the group consisting of PCR, NASBA, reverse transcription, and LAMP.

8. A microfluidic product for amplifying a nucleic acid, wherein:

a) said product comprises a first plate having at least one amplification chamber and a microfluidic assay circuit;

b) said product is manufactured by a process comprising a step of coveringly joining an optically transparent polyethylene terephthalate heat exchange film to said first plate with a sandwich comprising a double-sided ACA layer of pressure sensitive adhesive, thereby sealingly enclosing said amplification chamber, and c) said ACA layer in said product is further characterized as having at least one laser cutout configured to expose the internal surface of the heat exchange film forming the cap of said amplification chamber.

9. The microfluidic device of claim 8, further wherein said polyethylene terephthalate film and said ACA adhesive layer are supplied as roll stock and said process is a continuous process.

10. A microfluidic device for amplifying a nucleic acid comprising:

a) a first plate with a first surface and a second surface;

b) a first amplification chamber formed in said first surface;

c) a microfluidic assay fluid circuit fluidly connected to said first amplification chamber; and d) a heat exchange film covering and sealing over said first amplification chamber, said heat exchange film with interior surface facing said first surface of said first plate and with oppositely facing exterior surface, wherein said interior surface of said heat exchange film is an optically and UV transparent cyclic polyolefin roll stock film, and wherein said heat-exchange film is joined to said first plate by a double sided ACA adhesive layer with laser cutout to seal around but not cover said amplification chambers.

11. The microfluidic product of claim 10, wherein said device is configured for performing an enzymatic reaction selected from the group consisting of PCR, NASBA, reverse transcription, and LAMP.

12. A microfluidic product for amplifying a nucleic acid, wherein a) said product comprises a first plate having at least one amplification chamber and a microfluidic assay circuit;

b) said product is manufactured by a process comprising a step of coveringly joining an optically and UV transparent cyclic polyolefin heat exchange film to said first plate with a sandwich comprising a double-sided ACA layer of pressure sensitive adhesive, thereby sealingly enclosing said amplification chamber; and c) said ACA layer in said product is further characterized as having at least one laser cutout configured to expose the internal surface of the heat exchange film forming the cap of said amplification chamber.

* * * * *